(12) United States Patent
Hebeisen et al.

(10) Patent No.: US 7,547,699 B2
(45) Date of Patent: Jun. 16, 2009

(54) TETRACYCLIC 6 AZAPYRAZINOINDOLINES AS 5HT2C RECEPTOR AGONISTS FOR OBESITY

(75) Inventors: Paul Hebeisen, Basel (CH); Nathaniel Monck, Wokingham (GB); Hans Richter, Grenzach-Wyhlen (DE); Stephan Roever, Inzlingen (DE)

(73) Assignees: Hoffmann-La Roche Inc., Nutley, NJ (US); Vernalis Research Limited, Winnersh, Wokingham (GB)

( * ) Notice: Subject to any disclaimer, the term of this patent is extended or adjusted under 35 U.S.C. 154(b) by 325 days.

(21) Appl. No.: 11/412,501

(22) Filed: Apr. 26, 2006

(65) Prior Publication Data

US 2006/0252759 A1 Nov. 9, 2006

(30) Foreign Application Priority Data

May 3, 2005 (EP) .................................. 05103703

(51) Int. Cl.
*A01N 43/60* (2006.01)
(52) U.S. Cl. ....................... 514/250; 544/346
(58) Field of Classification Search ................. 544/346
See application file for complete search history.

(56) References Cited

U.S. PATENT DOCUMENTS

| | | | |
|---|---|---|---|
| 4,598,089 | A | 7/1986 | Hadvary et al. |
| 4,931,463 | A | 6/1990 | Barbier et al. |
| 4,983,746 | A | 1/1991 | Barbier et al. |
| 5,175,186 | A | 12/1992 | Barbier et al. |
| 5,245,056 | A | 9/1993 | Karph et al. |
| 5,246,960 | A | 9/1993 | Barbier et al. |
| 5,399,720 | A | 3/1995 | Karpf et al. |
| 6,004,996 | A | 12/1999 | Shah et al. |

FOREIGN PATENT DOCUMENTS

| | | |
|---|---|---|
| EP | 189577 | 12/1989 |
| EP | 185359 | 12/1991 |
| EP | 524495 | 10/1996 |
| EP | 443449 | 5/1997 |
| WO | WO99/34786 | 7/1999 |
| WO | WO 00/09122 | 2/2000 |
| WO | WO 00/09123 | 2/2000 |
| WO | WO 00/12510 | * 3/2000 |
| WO | WO 00/44753 | * 8/2000 |
| WO | WO 02/10169 | 2/2002 |
| WO | WO 03064423 | 8/2003 |
| WO | WO 2005000849 | 1/2005 |

OTHER PUBLICATIONS

Keller and Wahli: Trends Endocrin. Metab. 1993; 4: 291-296.
Macdonald and Lane: Current Biology vol. 5 pp. 618-621 (1995).
D. Hoyer, G. Engel and H.O. Kalkman, *European J. Pharmacol.*, 1985, 118, 13-23.
K. Schmuck, C. Ullmer, P. Engels and H. Lubbert, *FEBS Lett.*, 1994, 342, 85-90.
D. J. McKenna and S. J. Peroutka, *J. Neurosci.*, 1989, 9, 3482-90.

* cited by examiner

*Primary Examiner*—James O Wilson
*Assistant Examiner*—Brian McDowell
(74) *Attorney, Agent, or Firm*—George W. Johnston; Dennis P. Tramaloni; Samuel H. Megerditchian

(57) ABSTRACT

The present invention refers to chemical compounds of formula (I)

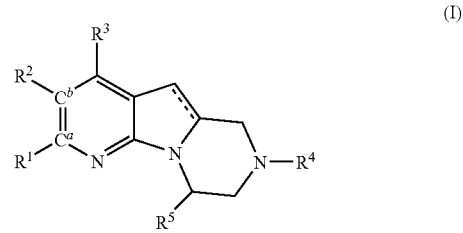

as well as pharmaceutically acceptable salts and esters thereof, wherein $R^1$ to $R^5$ have the significance given in claim 1. These compounds can be used for the preparation of medicaments.

17 Claims, No Drawings

TETRACYCLIC 6 AZAPYRAZINOINDOLINES AS 5HT2C RECEPTOR AGONISTS FOR OBESITY

PRIORITY TO RELATED APPLICATIONS

This application claims the benefit of European Application No. 05103703.4, filed May 3, 2005, which is hereby incorporated by reference in its entirety.

FIELD OF THE INVENTION

The present invention is directed to new chemical compounds in particular new fluorene derivatives, to processes and intermediates for their preparation, to pharmaceutical compositions containing them and to their medicinal use. The compounds of the present invention are useful in treating obesity and other disorders.

The invention is concerned particularly with compounds of formula

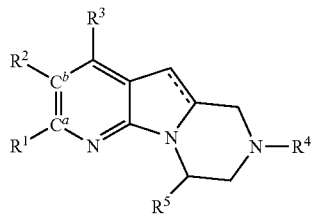

and pharmaceutically acceptable salts and esters thereof.

All documents cited or relied upon below are expressly incorporated herein by reference.

BACKGROUND

It has been recognized that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI), which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/noradrenalin reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

SUMMARY OF THE INVENTION

In an embodiment of the present invention, provided is a compound of formula

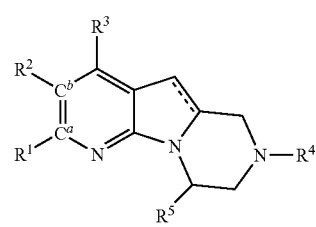

wherein

R$^1$ and R$^2$ form together with the carbon atoms C$^a$ and C$^b$ to which they are attached

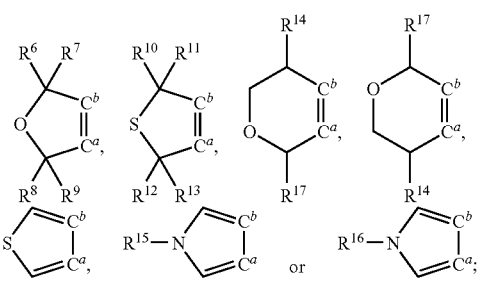

R$^3$ is hydrogen, alkyl or cycloalkyl;
R$^4$ is hydrogen, alkyl, cycloalkyl, alkylcarbonyl or cycloalkylcarbonyl;
R$^5$ is alkyl or cycloalkyl;
R$^6$ and R$^7$ are independently selected from hydrogen, alkyl, cycloalkyl, hydroxyalkyl and alkoxyalkyl;
R$^8$ and R$^9$ are independently selected from hydrogen, alkyl, cycloalkyl, hydroxyalkyl and alkoxyalkyl;
R$^{10}$ and R$^{11}$ are independently selected from hydrogen and alkyl;
R$^{12}$ and R$^{13}$ are independently selected from hydrogen and alkyl;
R$^{14}$ is hydrogen, alkyl, hydroxy or alkoxy;
R$^{15}$ is hydrogen, alkyl or cycloalkyl;
R$^{16}$ is hydrogen, alkyl or cycloalkyl;
R$^{17}$ is hydrogen, alkyl or cycloalkyl;

and pharmaceutically acceptable salts and esters thereof.

In another embodiment of the present invention, provided is a pharmaceutical composition, comprising a therapeutically effective amount of a compound according to formula I and a therapeutically inert carrier.

In a further embodiment of the present invention, provided is a method for the treatment and prophylaxis of disorders of the central nervous system, cardiovascular disorders, gastrointestinal disorders, diabetes insipidus, and sleep apnea, comprising the step of administering a therapeutically effective amount of a compound according to formula I to a patient in need thereof.

In a yet another embodiment of the present invention, provided is a process for the preparation of a compound of formula I, comprising one of the following reactions:

reacting a compound of formula

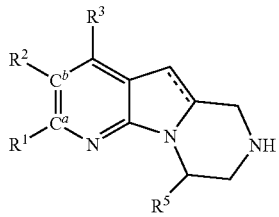

by reductive amination with aldehydes or ketones or by acylation with activated carbonic acid derivatives and reduction of the resulting amines by lithium aluminiumhydride in order to obtain a compound of formula (I)

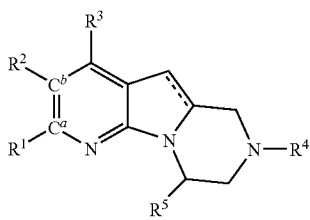
(I)

wherein $R^1$ to $R^5$ are defined above;

reduction of a compound of formula

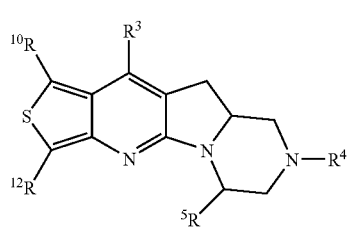

in order to obtain a compound of formula

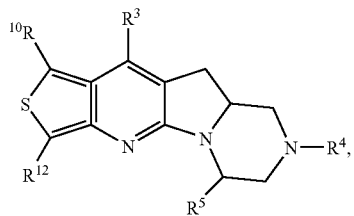

wherein $R^3$, $R^4$, $R^5$, $R^{10}$ and $R^{12}$ are defined above;

reduction of a compound of formula

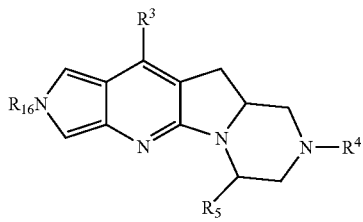

in order to obtain a compound of the formula

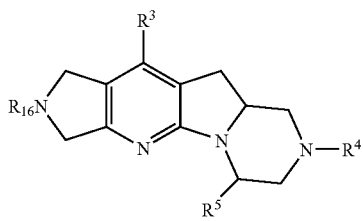

wherein $R^3$, $R^4$, $R^5$ and $R^{16}$ are defined above.

In a still further embodiment of the present invention, provided is a method for the treatment and prophylaxis of eating disorders and obesity, comprising the step of administering a therapeutically effective amount of a compound according to formula to a patient in need thereof.

In another embodiment of the present invention, provided is a method for the treatment and prophylaxis of disorders selected from diabetes mellitus, Type I diabetes, Type II diabetes, diabetes secondary to pancreatic disease, diabetes related to steroid use, Type III diabetes, hyperglycemia, diabetic complications and insulin resistance, comprising the step of administering a therapeutically effective amount of a compound according to formula I to a patient in need thereof.

In a yet still another embodiment of the present invention, provided is a method of treatment of obesity, comprising the step of administering a therapeutically effective amount of a compound according to formula I and a therapeutically effective amount of a lipase inhibitor to a patient in need thereof.

DETAILED DESCRIPTION

It is an embodiment of this invention to provide selective, directly acting 5-HT$_2$ receptor ligands for use in therapy and particularly for use as anti-obesity agents. It is a further embodiment of this invention to provide directly acting ligands selective for 5-HT$_{2B}$ and/or 5-HT$_{2C}$ receptors, for use in therapy and particularly for use as anti-obesity agents. It is a further embodiment of this invention to provide selective, directly acting 5-HT$_{2C}$ receptor ligands, preferably 5-HT$_{2C}$ receptor agonists, for use in therapy and particularly for use as anti-obesity agents.

The compounds of formula (I) are useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes may be diabetes secondary to pancreatic disease; or diabetes related to steroid use. The compounds of formula (I) are also useful in the treatment and/or prevention of the sequelae of hyperglycemia; in the treatment and/or prevention of diabetic complications; and in the treatment of insulin dependence.

The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

The present invention encompasses the use of compounds according to formula I for the acute and/or chronic treatment and/or prevention of disorders involving elevated plasma blood glucose, particularly the acute and/or chronic treatment of disorders involving elevated plasma blood glucose, and especially acute treatment of disorders involving elevated plasma blood glucose.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80-90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to exhaustion of the pancreas.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycemia, particularly NIDDM are urgently needed. Recent studies provided evidence that coagonism of PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4: 291-296, Macdonald and Lane: Current Biology Vol. 5 pp. 618-621 (1995)). The novel compounds of the present invention can be used as efficacious drugs for the treatment and prevention of diabetes, particularly of non-insulin dependent diabetes mellitus.

In the present description the term "alkyl", alone or in combination, signifies a straight-chain or branched-chain alkyl group with 1 to 8 carbon atoms, preferably a straight or branched-chain alkyl group with 1-4 carbon atoms. Examples of straight-chain and branched $C_1$-$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and cyclopentyl and particularly cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

The term "hydroxyalkyl", alone or in combination, signifies an alkyl group as previously defined, wherein one or several hydrogen atoms, preferably one hydrogen atom has been replaced by a hydroxyl group. Examples are hydroxymethyl, hydroxyethyl and 2-hydroxyethyl.

The term "carbonyl", alone or in combination, signifies a group of the formula —C(O)—.

The term "halogen" signifies fluorine, chlorine, bromine or iodine and preferably fluorine, chlorine or bromine and particularly fluorine and chlorine.

The term "carboxy", alone or in combination, signifies a —COOH group.

The term "cyano", alone or in combination, signifies a —CN group.

The term "oxy", alone or in combination, signifies an —O— group.

The term "pharmaceutically acceptable salts" refers to those salts which retain the biological effectiveness and properties of the free bases or free acids, which are not biologically or otherwise undesirable. Preferred are the salts which are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition "pharmaceutically acceptable salts" may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions.

The invention expressly includes pharmaceutically usable solvates of compounds according to formula I. The compounds of formula I can be solvated, e.g. hydrated. The solvation can be effected in the course of the manufacturing process or can take place, e.g. as a consequence of hygroscopic properties of an initially anhydrous compound of formula I (hydration). The term pharmaceutically acceptable salts also includes pharmaceutically usable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the pharmaceutically usable esters are compounds of formula I, wherein e.g. an hydroxy group can be esterified. Examples of such esters are formate, acetate, propionate, butyrate, isobutyrate, valerate, 2-methylbutyrate, isovalerate and N,N-dimethylaminoacetate.

The invention expressly includes prodrugs of compounds according to formula I. The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

Preferred are the compounds according to formula I and their pharmaceutically acceptable salts. Preferred salts are the hydrochloride salts. Particularly preferred are the compounds according to formula I.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom" (C*) means a carbon atom with four different substituents. According to the Cahn-Ingold-Prelog Convention the asymmetric carbon atom can be of the "R" or "S" configuration.

Preferred are chiral compounds of formula I. Preferred are those compounds of formula I, wherein the compound is of formula

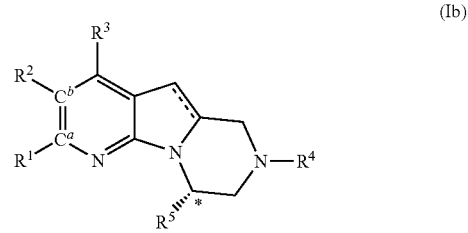

(Ib)

wherein the carbon atom C* is of the S configuration and $R^1$ to $R^5$ are defined as before.

Particularly preferred are those compounds according to formula I, wherein the compound is of formula

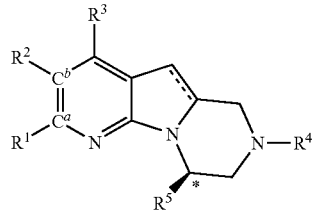
(Ia)

wherein the carbon atom C* is of the R configuration and $R^1$ to $R^5$ are defined as before.

The dotted line in formula I (marked as *) represents a carbon carbon single or a carbon carbon double bond

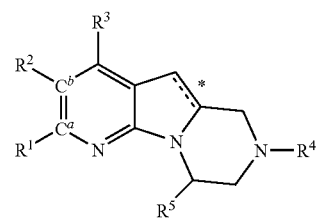
(I)

and, wherein $R^1$ to $R^5$ are defined as before. Accordingly, compounds of formula (I) are of one of the following formulae (II) and (III)

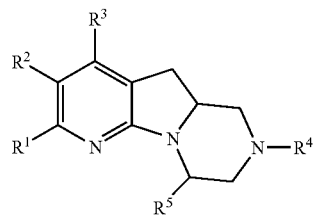
(II)

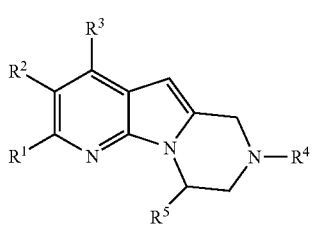
(III)

wherein $R^1$ to $R^5$ are defined as before.

Preferred compounds of formula I are those which are of formula III. Particularly preferred are compounds of formula I which are of formula II.

Further preferred are those compounds of formula (II), wherein the compound is of formula

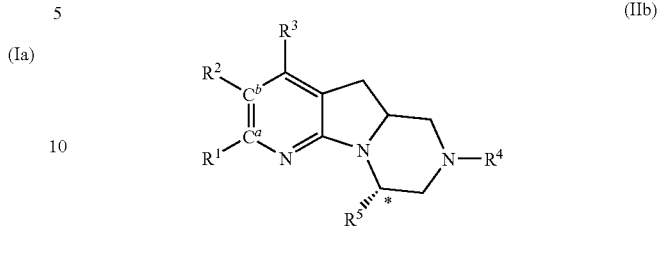
(IIb)

wherein the carbon atom C* to which $R^5$ is attached is of the S configuration and $R^1$ to $R^5$ are defined as before.

Particularly preferred are those compounds of formula II, wherein the compound is of formula

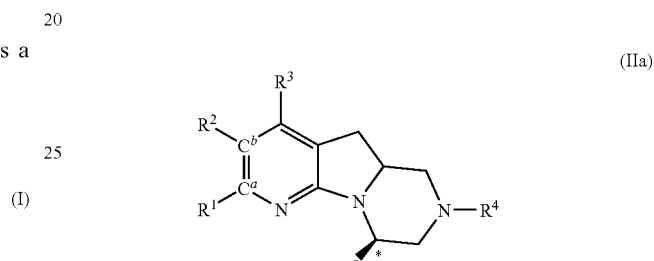
(IIa)

wherein the carbon atom C* to which $R^5$ is attached is of the R configuration and $R^1$ to $R^5$ are defined as before.

Further preferred are those compounds according to formula III, wherein the compound is of formula IIIb

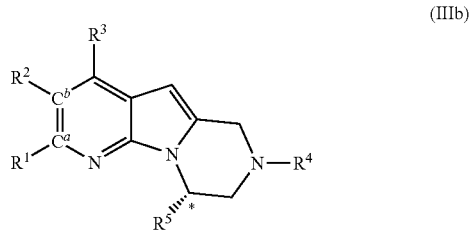
(IIIb)

wherein the carbon atom C* to which $R^5$ is attached is of the S configuration and $R^1$ to $R^5$ are defined as before.

Particularly preferred are those compounds of formula III, wherein the compound is of formula

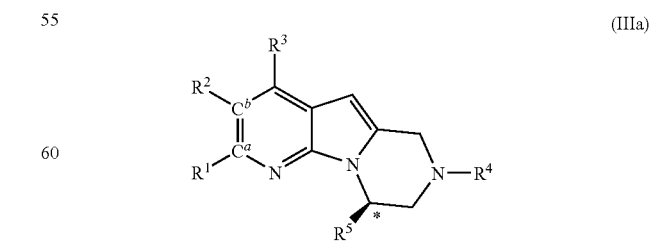
(IIIa)

wherein the carbon atom C* to which $R^5$ is attached is of the R configuration and $R^1$ to $R^5$ are defined as before.

Another preferred embodiment of the present invention is a compound according to formula I, wherein $R^4$ is hydrogen, methyl, ethyl or methylcarbonyl. Particularly preferred are those compounds, wherein $R^4$ is hydrogen.

Further preferred compounds according to formula I are those, wherein $R^3$ is hydrogen.

Other preferred compounds of formula I are those, wherein $R^5$ is methyl.

Compounds of the present invention are compounds according to formula I, wherein $R^1$ and $R^2$ form together with the carbon atoms $C^a$ and $C^b$ to which they are attached

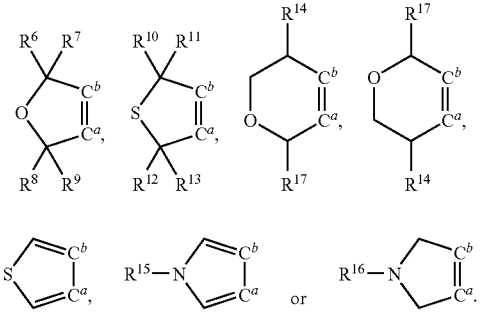

Compounds of formula I, wherein $R^1$ and $R^2$ form together with the carbon atoms $C^a$ and $C^b$ to which they are attached

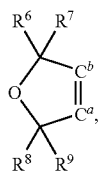

have the following formula

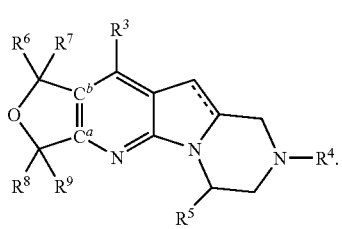

(IVa)

Compounds of formula I, wherein $R^1$ and $R^2$ form together with the carbon atoms $C^a$ and $C^b$ to which they are attached

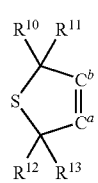

have the following formula

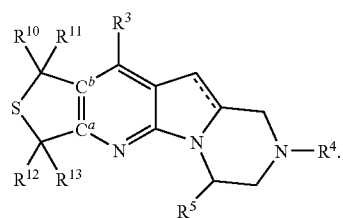

(IVb)

Compounds of formula I, wherein $R^1$ and $R^2$ form together with the carbon atoms $C^a$ and $C^b$ to which they are attached

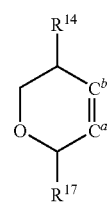

have the following formula

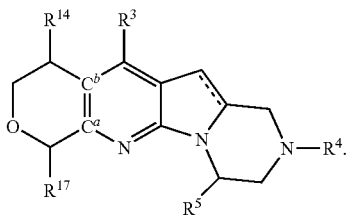

(IVc)

Compounds of formula I, wherein $R^1$ and $R^2$ form together with the carbon atoms $C^a$ and $C^b$ to which they are attached

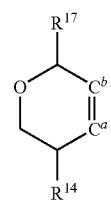

have the following formula

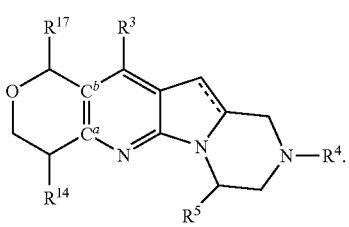

(IVd)

Compounds of formula I, wherein $R^1$ and $R^2$ form together with the carbon atoms $C^a$ and $C^b$ to which they are attached

have the following formula

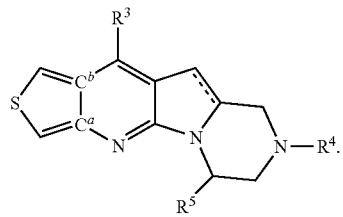

(IVe)

Compounds of formula I, wherein $R^1$ and $R^2$ form together with the carbon atoms $C^a$ and $C^b$ to which they are attached

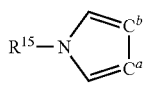

have the following formula

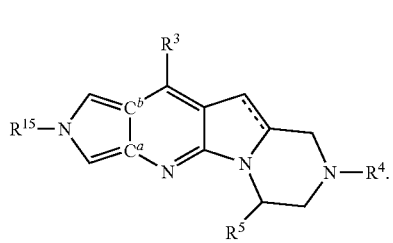

(IVf)

Compounds of formula I, wherein $R^1$ and $R^2$ form together with the carbon atoms $C^a$ and $C^b$ to which they are attached

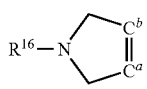

have the following formula

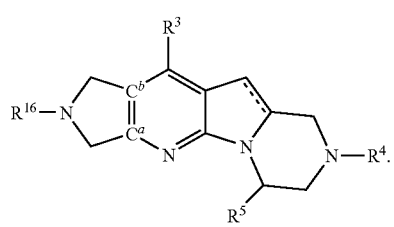

(IVg)

Preferred are compounds of formula I, wherein $R^1$ and $R^2$ form together with the carbon atoms $C^a$ and $C^b$ to which they are attached

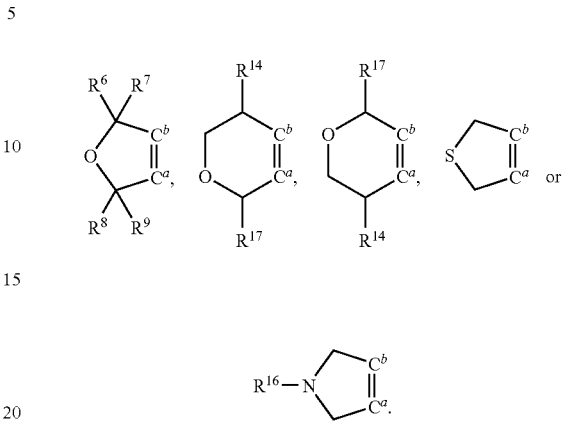

Particularly preferred are those compounds of formula I, wherein $R^1$ and $R^2$ form together with the carbon atoms $C^a$ and $C^b$ to which they are attached

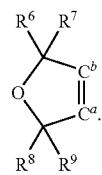

Further preferred are those compounds according to formula I, wherein the compound is of formula IVb.

Also preferred are those compounds of formula I, wherein the compound is of formula IVc.

Additionally preferred are those compounds according to formula I, wherein the compound is of formula IVd.

Another preferred embodiment of the present invention are those compounds according to formula I, wherein the compound is of formula IVe.

Further preferred are those compounds according to formula I, wherein the compound is of formula IVf.

Preferred are those compounds according to formula I, wherein the compound is of formula IVg.

Additionally preferred are those compounds of formula I, wherein $R^6$ and $R^7$ are independently selected from hydrogen and methyl.

Preferred are compounds of formula I, wherein $R^8$ and $R^9$ are independently selected from hydrogen, methyl, ethyl, propyl, isopropyl and cyclopropyl.

Further preferred are those compounds of formula I, wherein $R^{10}$, $R^{11}$, $R^{12}$ and $R^{13}$ are hydrogen.

Also preferred are compounds of formula I, wherein $R^{14}$ is hydrogen, hydroxyl or methoxy.

Another preferred embodiment of the present invention are compounds of formula I, wherein $R^{15}$ is cyclopropyl.

Preferred are compound of formula I, wherein $R^{16}$ is cyclopropyl.

Further preferred are those compounds of formula I, wherein $R^{17}$ is hydrogen.

Examples of preferred compounds of formula I are
1. (5R,8aR)-5-Methyl-1,3,5,6,7,8,8a,9-octahydro-2-oxa-4,4b,7-triaza-cyclopenta[b]fluorene;
2. (5R,8aS)-5-Methyl-1,3,5,6,7,8,8a,9-octahydro-2-oxa-4,4b,7-triaza-cyclopenta[b]fluorene;
3. (R)-5-Methyl-1,3,5,6,7,8-hexahydro-2-oxa-4,4b,7-triaza-cyclopenta[b]fluorene;
4. 5-Methyl-1,3,5,6,7,8,8a,9-octahydro-2-oxa-4,4b,7-triaza-cyclopenta[b]fluorene;
5. (5R,8aR)-5,7-Dimethyl-1,3,5,6,7,8,8a,9-octahydro-2-oxa-4,4b,7-triaza-cyclopenta[b]fluorene;
6. (5R,8aR)-7-Ethyl-5-methyl-1,3,5,6,7,8,8a,9-octahydro-2-oxa-4,4b,7-triaza-cyclopenta[b]fluorene;
7. 1-((5R,8aR)-5-Methyl-3,5,6,8,8a,9-hexahydro-1H-2-oxa-4,4b,7-triaza-cyclopenta[b]fluoren-7-yl)-ethanone;
8. (5R,8aR)-3,5-Dimethyl-1,3,5,6,7,8,8a,9-octahydro-2-oxa-4,4b,7-triaza-cyclopenta[b]fluorene;
9. (3S,5R,8aR)-3,5-Dimethyl-1,3,5,6,7,8,8a,9-octahydro-2-oxa-4,4b,7-triaza-cyclopenta[b]fluorene;
10. (3R,5R,8aR)-3,5-Dimethyl-1,3,5,6,7,8,8a,9-octahydro-2-oxa-4,4b,7-triaza-cyclopenta[b]fluorene;
11. (3S,5R,8aR)-3-Ethyl-5-methyl-1,3,5,6,7,8,8a,9-octahydro-2-oxa-4,4b,7-triaza-cyclopenta[b]fluorene;
12. (3R,5R,8aR)-3-Ethyl-5-methyl-1,3,5,6,7,8,8a,9-octahydro-2-oxa-4,4b,7-triaza-cyclopenta[b]fluorene;
13. (3S,5R,8aR)-5-Methyl-3-propyl-1,3,5,6,7,8,8a,9-octahydro-2-oxa-4,4b,7-triaza-cyclopenta[b]fluorene;
14. (3R,5R,8aR)-5-Methyl-3-propyl-1,3,5,6,7,8,8a,9-octahydro-2-oxa-4,4b,7-triaza-cyclopenta[b]fluorene;
15. (3S,5R,8aR)-3-Isopropyl-5-methyl-1,3,5,6,7,8,8a,9-octahydro-2-oxa-4,4b,7-triazacyclopenta[b]fluorene;
16. (3R,5R,8aR)-3-Isopropyl-5-methyl-1,3,5,6,7,8,8a,9-octahydro-2-oxa-4,4b,7-triaza-cyclopenta[b]fluorene;
17. (3S,5R,8aR)-3-Cyclopropyl-5-methyl-1,3,5,6,7,8,8a,9-octahydro-2-oxa-4,4b,7-triaza-cyclopenta[b]fluorene;
18. (3R,5R,8aR)-3-Cyclopropyl-5-methyl-1,3,5,6,7,8,8a,9-octahydro-2-oxa-4,4b,7-triaza-cyclopenta[b]fluorene;
19. (5R,8aR)-3,3,5-Trimethyl-1,3,5,6,7,8,8a,9-octahydro-2-oxa-4,4b,7-triaza-cyclopenta[b]fluorene;
20. (5R,8aR)-1,5-Dimethyl-1,3,5,6,7,8,8a,9-octahydro-2-oxa-4,4b,7-triaza-cyclopenta[b]fluorene;
21. (5R,8aR)-1,1,5-Trimethyl-1,3,5,6,7,8,8a,9-octahydro-2-oxa-4,4b,7-triaza-cyclopenta[b]fluorene;
22. (5R,8aR)-1,3,5-Trimethyl-1,3,5,6,7,8,8a,9-octahydro-2-oxa-4,4b,7-triaza-cyclopenta[b]fluorene;
23. (5R,8aR)-1,1,3,3,5-Pentamethyl-1,3,5,6,7,8,8a,9-octahydro-2-oxa-4,4b,7-triaza-cyclopenta[b]fluorene;
24. (5R,8aR)-5,10-Dimethyl-1,3,5,6,7,8,8a,9-octahydro-2-oxa-4,4b,7-triaza-cyclopenta[b]fluorene;
25. (4R,11aR)-4-Methyl-1,3,4,6,8,9,11,11a-octahydro-2H-7-oxa-2,4a,5-triaza-benzo[b]fluorene;
26. (4R,11aR)-4-Methyl-1,3,4,6,8,9,11,11a-octahydro-2H-7-oxa-2,4a,5-triaza-benzo[b]fluorene;
27. (4R,8R,11aR)-4,9-Dimethyl-1,2,3,4,6,9,11,11a-octahydro-7H-8-oxa-2,4a,5-triaza-benzo[b]fluorene;
28. (4R,8S,11aR)-4,9-Dimethyl-1,2,3,4,6,9,11,11a-octahydro-7H-8-oxa-2,4a,5-triaza-benzo[b]fluorene;
29. ((3R,5R,8aR)-5-Methyl-1,3,5,6,7,8,8a,9-octahydro-2-oxa-4,4b,7-triaza-cyclopenta[b]fluoren-3-yl)-methanol;
30. (3R,5R,8aR)-3-Methoxymethyl-5-methyl-1,3,5,6,7,8,8a,9-octahydro-2-oxa-4,4b,7-triaza-cyclopenta[b]fluorene;
31. (5R,8aR)-2-Cyclopropyl-5-methyl-2,3,5,6,7,8,8a,9-octahydro-1H-2,4,4b,7-tetraaza-cyclopenta[b]fluorene;
32. (5R,8aR)-2-Cyclopropyl-5-methyl-5,6,7,8,8a,9-hexahydro-2H-2,4,4b,7-tetraaza-cyclopenta[b]fluorene;
33. (5R,8aR)-5-Methyl-1,3,5,6,7,8,8a,9-octahydro-2-thia-4,4b,7-triaza-cyclopenta[b]fluorene; and
34. (5R,8aR)-5-Methyl-5,6,7,8,8a,9-hexahydro-2-thia-4,4b,7-triaza-cyclopenta[b]fluorene.

Examples of particularly preferred compounds of formula I are (5R,8aR)-5-Methyl-1,3,5,6,7,8,8a,9-octahydro-2-oxa-4,4b,7-triaza-cyclopenta[b]fluorene;

(5R,8aR)-5,7-Dimethyl-1,3,5,6,7,8,8a,9-octahydro-2-oxa-4,4b,7-triaza-cyclopenta[b]fluorene;

(5R,8aR)-3,5-Dimethyl-1,3,5,6,7,8,8a,9-octahydro-2-oxa-4,4b,7-triaza-cyclopenta[b]fluorene;

(3S,5R,8aR)-3,5-Dimethyl-1,3,5,6,7,8,8a,9-octahydro-2-oxa-4,4b,7-triaza-cyclopenta[b]fluorene;

(3R,5R,8aR)-3,5-Dimethyl-1,3,5,6,7,8,8a,9-octahydro-2-oxa-4,4b,7-triaza-cyclopenta[b]fluorene;

(3S,5R,8aR)-3-Ethyl-5-methyl-1,3,5,6,7,8,8a,9-octahydro-2-oxa-4,4b,7-triaza-cyclopenta[b]fluorene;

(3S,5R,8aR)-5-Methyl-3-propyl-1,3,5,6,7,8,8a,9-octahydro-2-oxa-4,4b,7-triaza-cyclopenta[b]fluorene;

(3S,5R,8aR)-3-Isopropyl-5-methyl-1,3,5,6,7,8,8a,9-octahydro-2-oxa-4,4b,7-triaza-cyclopenta[b]fluorene;

(3S,5R,8aR)-3-Cyclopropyl-5-methyl-1,3,5,6,7,8,8a,9-octahydro-2-oxa-4,4b,7-triaza-cyclopenta[b]fluorene;

(5R,8aR)-3,3,5-Trimethyl-1,3,5,6,7,8,8a,9-octahydro-2-oxa-4,4b,7-triaza-cyclopenta[b]fluorene;

(5R,8aR)-1,1,5-Trimethyl-1,3,5,6,7,8,8a,9-octahydro-2-oxa-4;4b,7-triaza-cyclopenta[b]fluorene;

(4R,11aR)-4-Methyl-1,3,4,6,8,9,11,11a-octahydro-2H-7-oxa-2,4a,5-triaza-benzo[b]fluorene;

(4R,11aR)-4-Methyl-1,3,4,6,8,9,11,11a-octahydro-2H-7-oxa-2,4a,5-triaza-benzo[b]fluorene;

(5R,8aR)-2-Cyclopropyl-5-methyl-2,3,5,6,7,8,8a,9-octahydro-1H-2,4,4b,7-tetraaza-cyclopenta[b]fluorene; and (5R,8aR)-5-Methyl-1,3,5,6,7,8,8a,9-octahydro-2-thia-4,4b,7-triaza-cyclopenta[b]fluorene.

Processes for the manufacture of the compounds according to formula I are an embodiment of the present invention. The substituents and indices used in the following schemes have the significance given above unless indicated to the contrary.

General procedures for the construction of tetracyclic fluorenes. (I)1 (Scheme1): The preparation of different fluorenes derivatives is described in e.g. WO 2003064423 A1 and WO 2005000849 A1.

Compounds of formula (I) are sub grouped purely for clarity into compounds of general formulas (I)a1-k1 in which the substituents R3-R17 are defined as before.

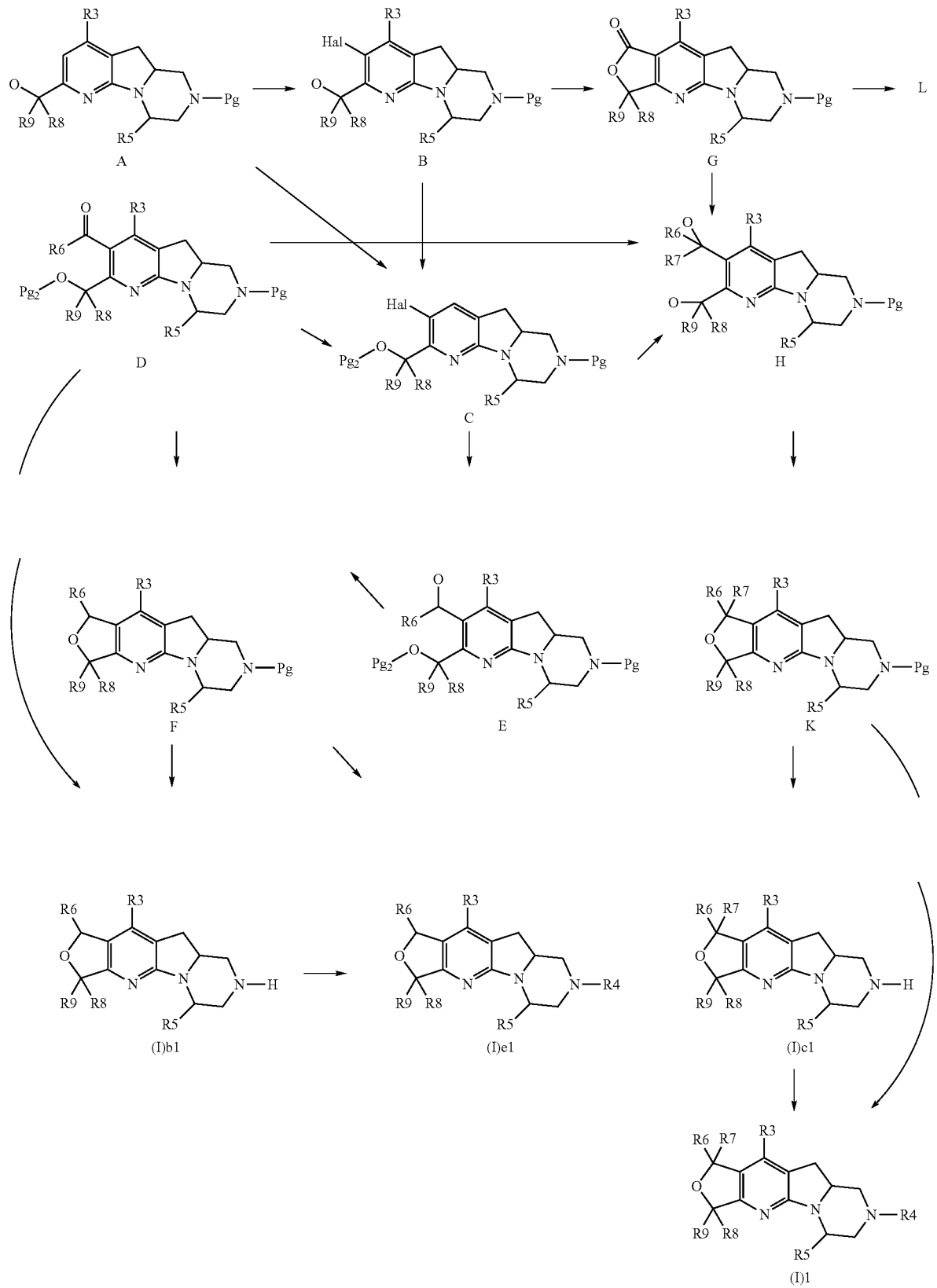
Scheme 1

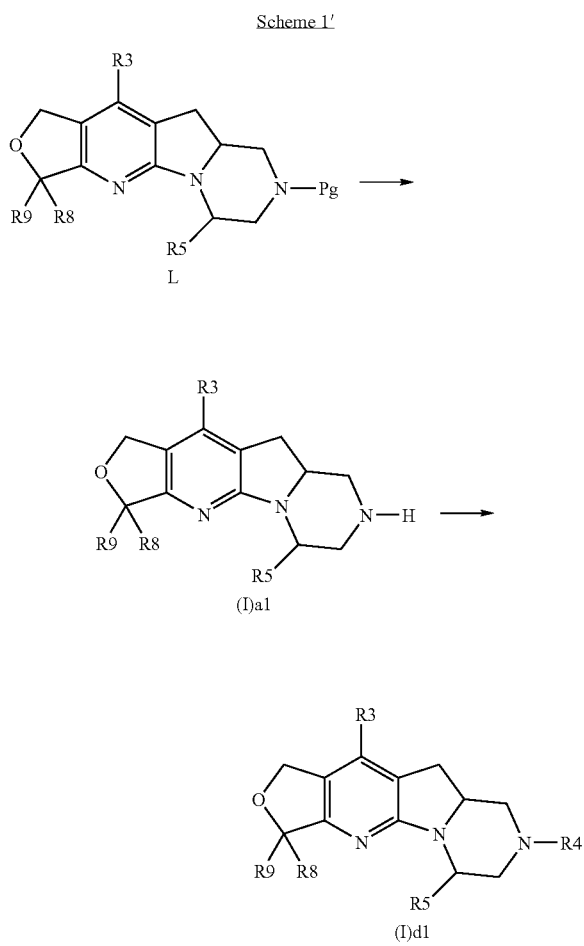

Scheme 1'

A compound of the general structure A (the synthesis A is described in the above mentioned patent applications including the control of the stereochemistry in the case of R8 unequal R9 in particular R9=H in the patent applications in which the groups R3 to R9 are defined as above and Pg means a suitable amine protecting group such as e.g. alkylcarbamates in particular tert-butylcarbamate) can be reacted with appropriate halogenating agents e.g. N-halosuccinimides, in which the term halo means chlorine, bromine or iodine, in particular N-bromosuccinimde in a suitable solvent e.g. exemplified ethers, preferably cyclic ethers in particular tetrahydrofuran, to yield a compound of the general structure B.

The alcohol group of the compounds of the general structure B can be protected in ways well described in the literature, such as ether preferably as silylether in particular as trialkylsilylether such as exemplified by tert-butyldimethylsilyl or thexyldimethylsily ether to give rise to a compound of the general structure C. The sequence of the halogenation reaction and the alcohol protection can be inverted such that the compound of the general structure A can first be protected as ether and in a second step halogenated to yield the compound of the general structure C.

The compound of structure C can be metalated by suitable metalating agents such as organo metal compounds preferably organo lithium compounds in particular tert-butyllithium in suitable solvents such as ethers, alkanes and preferably aromatics in particular toluene and reacted with carbonyl compounds such as aldehydes to yield a compound of the general formula E or ketones to yield a compound of the general structure H.

Alternatively the metalated species can be reacted with amides, preferably dialkylamides in particular dimethylformamide, dimethylacetamide or N-alkyl-N-alkoxyamides in particular Weinreb amides, to yield a compound of the general structure D. An alternative access to compounds of the general formula D consists of oxidation of compounds of the general formula E with appropriate oxidants such as the ones well described for the purpose of oxidizing secondary alcohols to ketones in particular metal oxides preferably manganese dioxide in appropriate solvents such as alkanes haloalkanes and esters, preferably dichloromethane.

Addition of organo metal compounds preferably organo magnesium and organo lithium compounds to compounds of the general structure D results again in compounds of the general structure H. This particular sequence of steps allows access to variants of compounds of the general structure G in which the groups R6 and R7 can be independently chosen.

Compounds of the general structure D can be deprotected selectively at oxygen. In the preferred case of Pg2 being represented by a silyl ether, selective desilylation can typically be achieved in the presence of fluorides such as represented by metal fluorides or (alkyl)$_n$ ammonium fluorides (n=0 to 4) preferably in particular caesium fluoride and ammonium fluoride in appropriate solvents such as alcohols, ethers or amides in particular tetrahydrofurane, methanol or dimethylformamide. The resulting intermediary formyl or keto alcohol exists in equilibrium with its ring tautomeric hemi acetal or hemi ketal respectively. In one aspect of the present invention addition of appropriate reducing agents such as metal hydrides in particular complex borohydrides and preferably sodium cyanoborohydride results in formation of compounds of the general formula F. A particular aspect of this general protocol consists of the conservation of stereochemistry at the carbon atom carrying the R8 and R9 substituents in case R8 being unequal R9. Alternatively compounds of the general formula D can be transformed into compounds of the general formula (I)b by treatment with suitable reducing agents such as silanes, in particular triethylsilane, in the presence of a suitable acid for example trifluoroacetic acid.

An alternative access to compounds of the general formula D consists of oxidation of compounds of the general formula E with appropriate oxidants such as the ones well described for the purpose of oxidizing secondary alcohols to ketones in particular metal oxides preferably manganese dioxide in appropriate solvents such as alkanes haloalkanes and esters, preferably dichloromethane.

Compounds of the general formula F can be transformed to compounds of formula (I)b1 by removal of the protective group Pg in ways well described in the literature. Alternatively the protective group can be transformed into a group R4 e.g. by reduction of a tert-butyloxycarbonyl protective group into a methyl group by reduction with appropriate reducing agents such as metal hydrides in particular lithium aluminium hydride, to produce compounds of the formula (I)e1.

Introduction of substituents R4 can be accomplished by standard methods such as reductive amination with aldehydes or ketones or by acylation with activated carbonic acid derivatives and reduction of the resulting amides by lithium aluminiumhydride.

In a further aspect of the current invention construction of the tetracyclic fluorenes is effected by palladium catalyzed carbonylation.

Compounds of the general formula B can be transformed to compounds of the general formula G in analogy to methods described in the literature, in particular by transition metal cat carbonylation in appropriate solvents such as alcohols, ethers and esters preferably by palladium catalyzed carbonylation in methanol.

Transformation of compounds of the general formula G to compounds of the general formula L can be achieved by reduction with appropriate reducing agents such as exemplified by low valent metal salts, metal hydrides or complex borohydrides, preferably lithium borohydride in the presence of suitable activating agents such as alkylating, acylating or silylating agents preferably trimethylsilyl chloride.

Compounds of the general formula L can be transformed to compounds of formula (I)a by removal of the protective group Pg. in ways well described in the literature. Alternatively the protective group can be transformed into a group R4 e.g. by reduction of a tert-butyloxycarbonyl protective group into a methyl group by reduction with appropriate reducing agents such as metal hydrides in particular lithium aluminium hydride to produce compounds of formula (I)d1.

Introduction of substituents R4 can further be accomplished by standard methods such as reductive amination with aldehydes or ketones or by acylation with activated carbonic acid derivatives and reduction of the resulting amides by lithium aluminiumhydride In a further aspect of the present invention construction of the tetracyclic fluorenes (I) can be effected starting from diols, and removing the elements of water.

For example compounds of the general formula H can be dehydrated in the presence of suitable dehydrating agents exemplified by, but not restricted to, such reagents as typically used in Mitsunobu reactions such as the combination of a phosphine, in particular triphenylphosphine and an azo compound such as a dialkyl azodicarboxylate in particular di-tert-butyl azodicarboxylate to yield compounds of the general formula K which can be transformed to compounds of the general formula (I)c1 and (I)f1 by the above mentioned methods.

An alternative access to compounds of the general formula H is outlined in scheme 2.

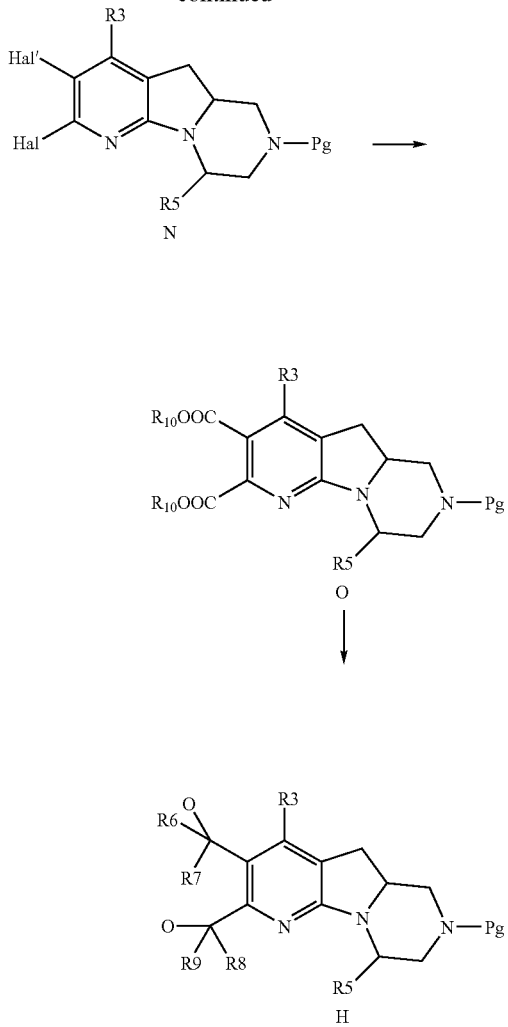

A compound of the general formula M in which the substituent denoted as Hal means a chlorine bromine or iodine atom can be halogenated to yield compounds of the general formula N in the same manner as described above for the conversion of compounds of the general formula A to compounds of the general formula B. Compounds of the general formula N can be doubly carbonylated with carbonmonoxide in the presence of a transition metal catalyst such as palladium acetate in a suitable solvent such as methanol to yield compounds of the general formula O. Reaction with excess of organo metal compounds such as organolithium compounds or Grignard compounds results in the formation of compounds of the general formula H. Compounds of the general formula H in which the groups R6-R9 are represented by hydrogen can be obtained from compounds of the general formula O by reduction with suitable reducing agents such as metal hydrides for instance complex borohydrides in particular lithium borohydride.

General procedure for the synthesis of thieno and dihydrothieno compounds
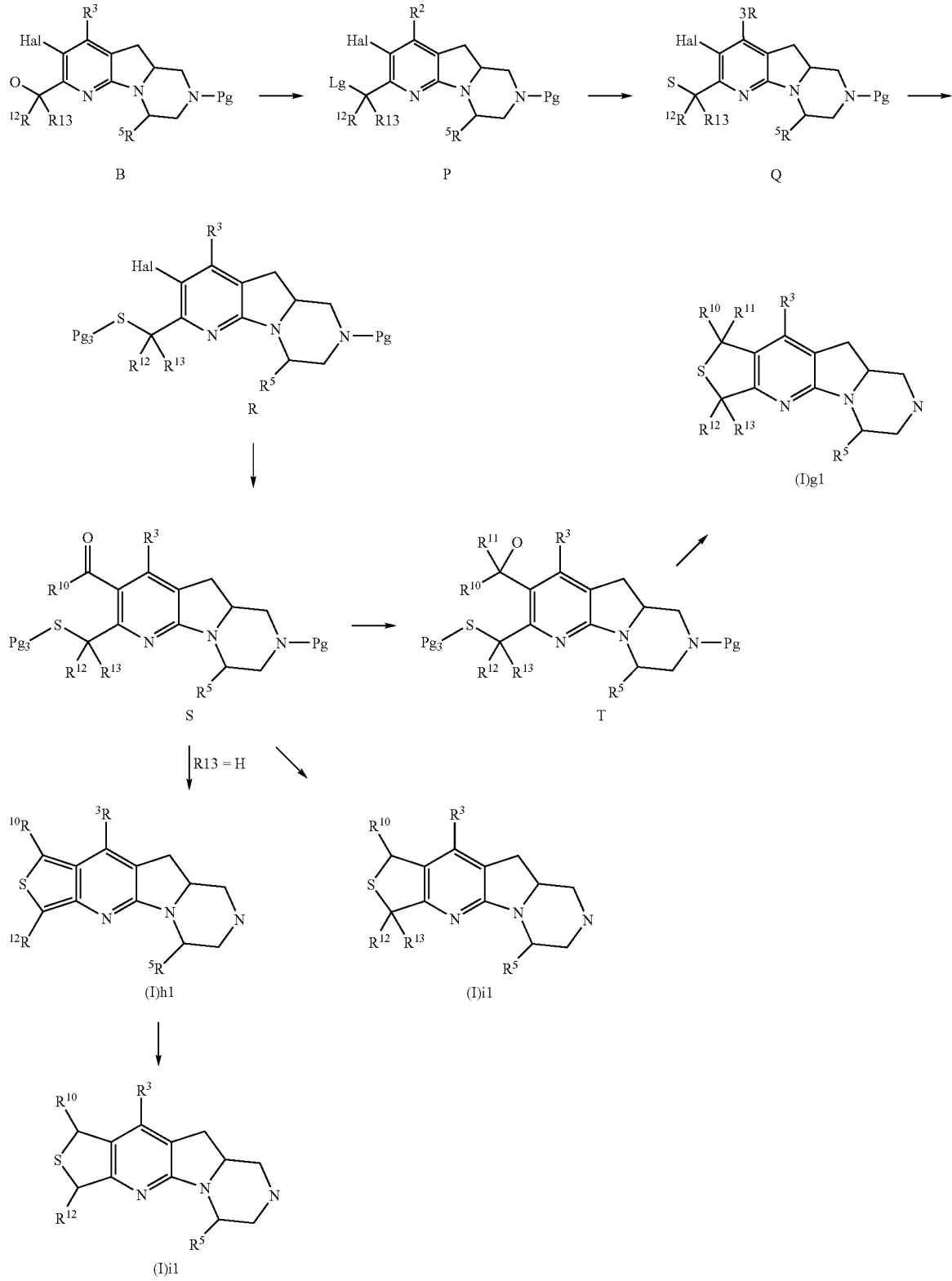
Scheme 3

The hydroxyl group in a compound of the general formula B can be transformed into a leaving group (Lg) by methods known in the art such as by reaction with sulfonyl halides in particular toluolsulfonyl chloride and methansulfonyl chloride in a suitable solvent in the presence of a base such as a tertiary amine. Alternatively the hydroxyl group in a compound of the general formula B can be transformed into a halogen leaving group by reaction with a phosphine such as a triarylphosphine in particular triphenylphosphine in presence of a tetrahalomethane such as carbontetrachloride or carbontetrabromide.

The intermediate of the general formula P can be transformed into a compound of the general formula Q by well known methods such as by reaction with thio compounds for example thiourea or thioacetic acid followed by basic hydrolysis of the formed thiouronium salts or thio acetates.

The mercapto group in the compound of the general formula Q can then be protected by introduction of a suitable protective group Pg3 such as an arlymethyl group for instance a benzyl group preferably by a protective group that is concomitantly removed together with the nitrogen protective group (Pg) such as a triarylmethyl group in particular a trityl group using for instance triphenylchloromethane in combination with a suitable base such as a trialkylamine in particular triethylamine or N-tritylpyridinium tetrafluoroborate to obtain a compound of the general formula R. By the same procedures as described above the compounds of the general formula R can be metalated and reacted with carbonyl compounds to obtain compounds of the general formula S and T. A compound of the general formula S can be treated with suitable acids to effect the removal of both protective groups for instance trifluoroacetic acid or formic acid to obtain a compound of the general type (I)h1 in the case of at least one of R12 or R13 being hydrogen. In the case of both R12 and R13 differing from hydrogen the compound of the general formula S can under otherwise similar conditions as for transformation to (I)h1 be transformed to a compound of the general type (I)j1 in the presence of a suitable reducing agent such as formic acid or a silane for example a trialkylsilane in particular triethylsilane. A compound of the general formula T can be transformed into a compound of the general type (I)g1 by treatment with acids useful for the removal of both protective groups and the abstraction of the elements of water, such as trifluoroacetic acid or formic acid. Reduction of a compound of the general type (I)h1 can be achieved after protection of the piperazine as the Boc derivative with suitable reducing agents such as silanes in particular polymethylhydroxy silane in the presence of metal catalysts such as palladium salts in particular palladium acetate and a fluoride source such as a salt of hydrofluoric acid, in particular potassium fluoride. Removal of the Boc protective group yields a compound of the general type (I)i1. The transformation of compounds of the general formula (I)g1, (I)h1, (I)i1 and (I)j1 to compounds bearing a group R4 that differs from H can be achieved in analogy to the methods described above for the transformation of compounds of the general type (I)a1, (I)b1, and (I)c1 to compounds of the general type (I)d1, (I)e1, and (I)f1 respectively.

General synthesis of pyrrolo and pryrrolino pyridines (I)k1, (I)l1 (scheme 4)

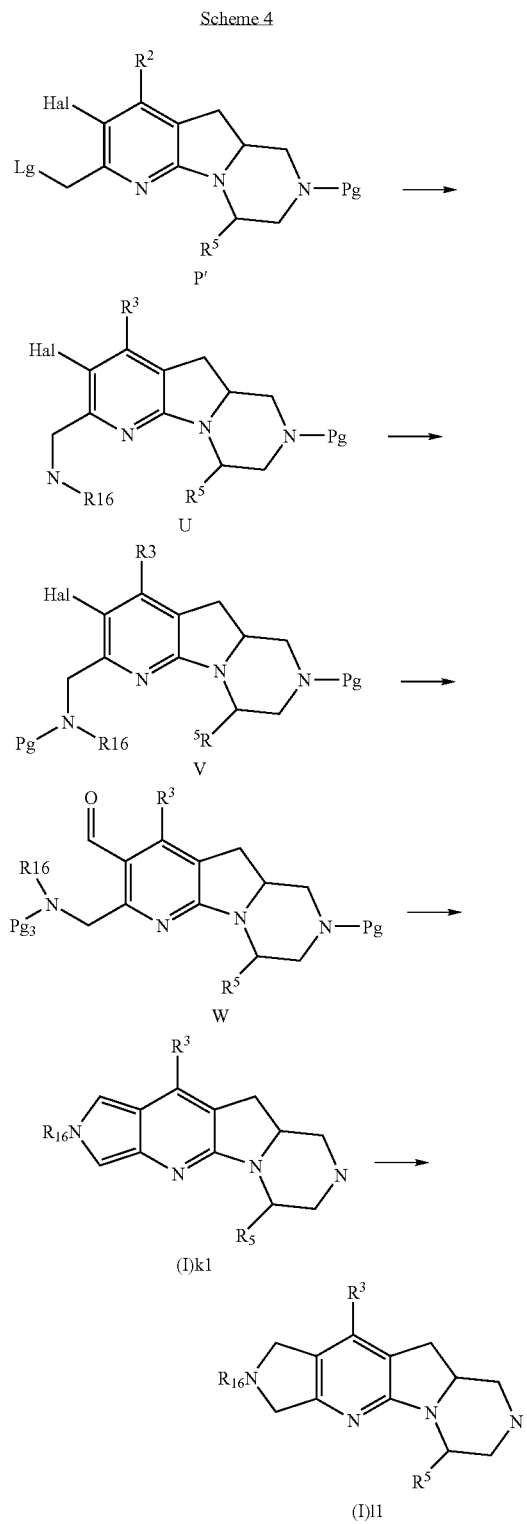

A compound of the general formula P'can be reacted with primary amines in a suitable solvent such as tetrahydrofurane to yield a compound of the general formula U which can be transformed into a compound of the general formula V by introduction of a protective group Pg preferably of the same nature as the protective group on the piperazine nitrogen. Conversion of a compound of the general formula V to a compound of the general formula W can be achieved in analogy to the methods mentioned above for the transformation of compounds of the general formula C to compounds of the general formula D. Removal of the protective groups Pg for instance in the case of Pg represented by the Boc protective group using acids such as trifluoroacetic acid or formic acid results in the formation of compounds of the general formula (I)k1. Reduction of compounds of the general formula (I)k1 to compounds of the general formula (I)l1 can be achieved for instance by hydrogenolysis in suitable solvents such as aqueous acids in particular aqueous acetic acid in the presence of a suitable catalyst for example palladium on charcoal. The transformation of compounds of the general formula (I)k1 and (I)l1 to compounds bearing a group R4 that differs from H can be achieved in analogy to the methods described above for the transformation of compounds of the general type (I)a1, (I)b1 and (I)c1 to compounds of the general type (I)d1, (I)e1 and (I)f1 respectively.

General Synthesis of Tetrahydropyrano Pyridines
General Synthesis of Compounds Type (I)m1 (Scheme 5)

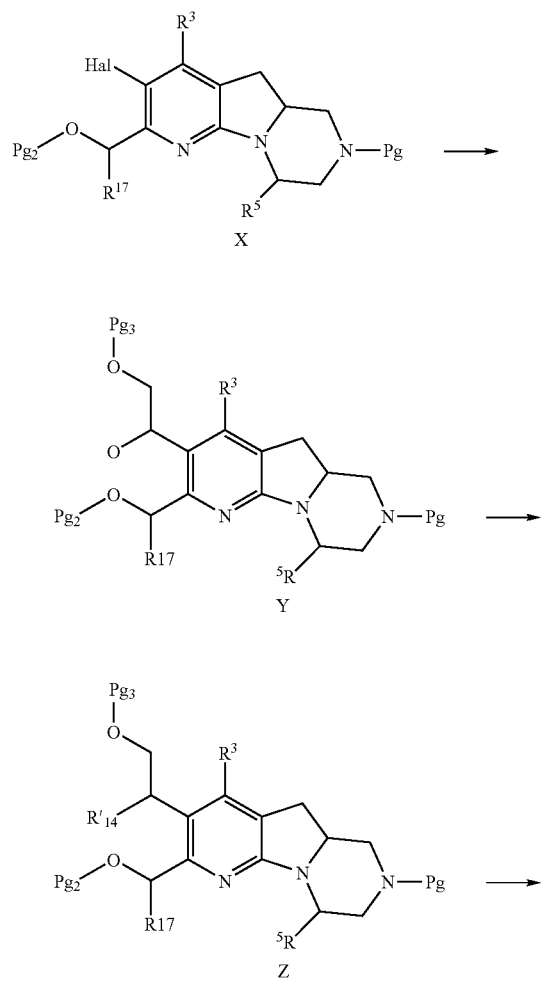

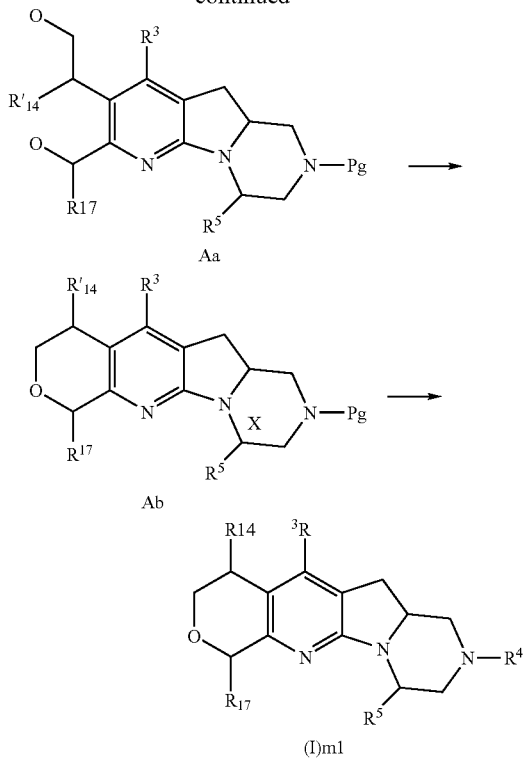

A compound of the general formula X can be metalated as described above for the metalation of compounds of the general formula C and reacted with protected 2-hydroxyacetaldehyde to yield a compound of the general formula Y. The protective group Pg3 can for instance be represented by ethers such as alkyl ethers, arylalkyl ethers or silyl ethers preferably tert-butyldimethylsilyl ether. The compounds of the general formula Y can be alkylated with appropriate alkylating reagents such as alkyl halides, alkyl triflates or trialkyoxonium tetrafluoroborates in an inert solvent in the presence of a suitable base such as sodium hydride. The secondary alcohol present in the compound of the general formula Y can be transformed into a tertiary alcohol by well known methods for example oxidation to a keton using a suitable oxidizing agent for example manganese dioxide and subsequent addition of alkyl metal compounds such as Grignard compounds. In one aspect of the invention the hydroxy function in compounds of the general formula Y and in tertiary alcohol analogs derived thereof can be replaced by hydrogen for instance by catalytic hydrogenation. In an other aspect of the invention the hydroxy function in compounds of the general formula Y can be protected orthogonally with respect to the other two oxygen protective groups, for example in the case of Pg2 and Pg3 being represented by silylethers orthogonal protection can be achieved by a methoxymethylether, to obtain compounds of the general formula Z in which the group R'14 has the meaning defined above for R14 including a protected hydroxy function. The compounds of the general formula Z can be transformed into compounds of the general formula Aa by selective removal of the protective groups Pg2 and Pg3 for instance in the case of Pg2 and Pg3 being represented by silylethers in the presence of a fluoride source such as salts of hydrofluoric acid for instance tetrabutylammonium fluoride or ammonium fluoride in a suitable solvent such as alcohols or ethers, preferably tetrahydrofurane or methanol. Transformation to a compound of the general formula Ab can be accomplished in the presence of suitable dehydrating agents exemplified by, but not restricted to, such reagents as typically used in Mitsunobu reactions such as the combination of a phosphine, in particular triphenylphosphine and an azo compound such as a dialkyl azodicarboxylate in particular di-tertbutyl azodicarboxylate. Removal of the nitrogen protective group Pg and subsequent introduction of a group R4 differing from hydrogen or alternatively, direct transformation of the nitrogen protective group Pg to such a group can be achieved by methods described for analogous transformations above to yield a compound of the general formula (I)m1. In the case of R'14 representing a protected hydroxy function this protective group is preferentially removed together with the nitrogen protective group for instance a methoxymethyl-ether protective group is cleaved concomitantly with the N-Boc protective group by acids such as trifluoroacetic acid or formic acid.

General synthesis of compounds type (I)n1 (Scheme 6)

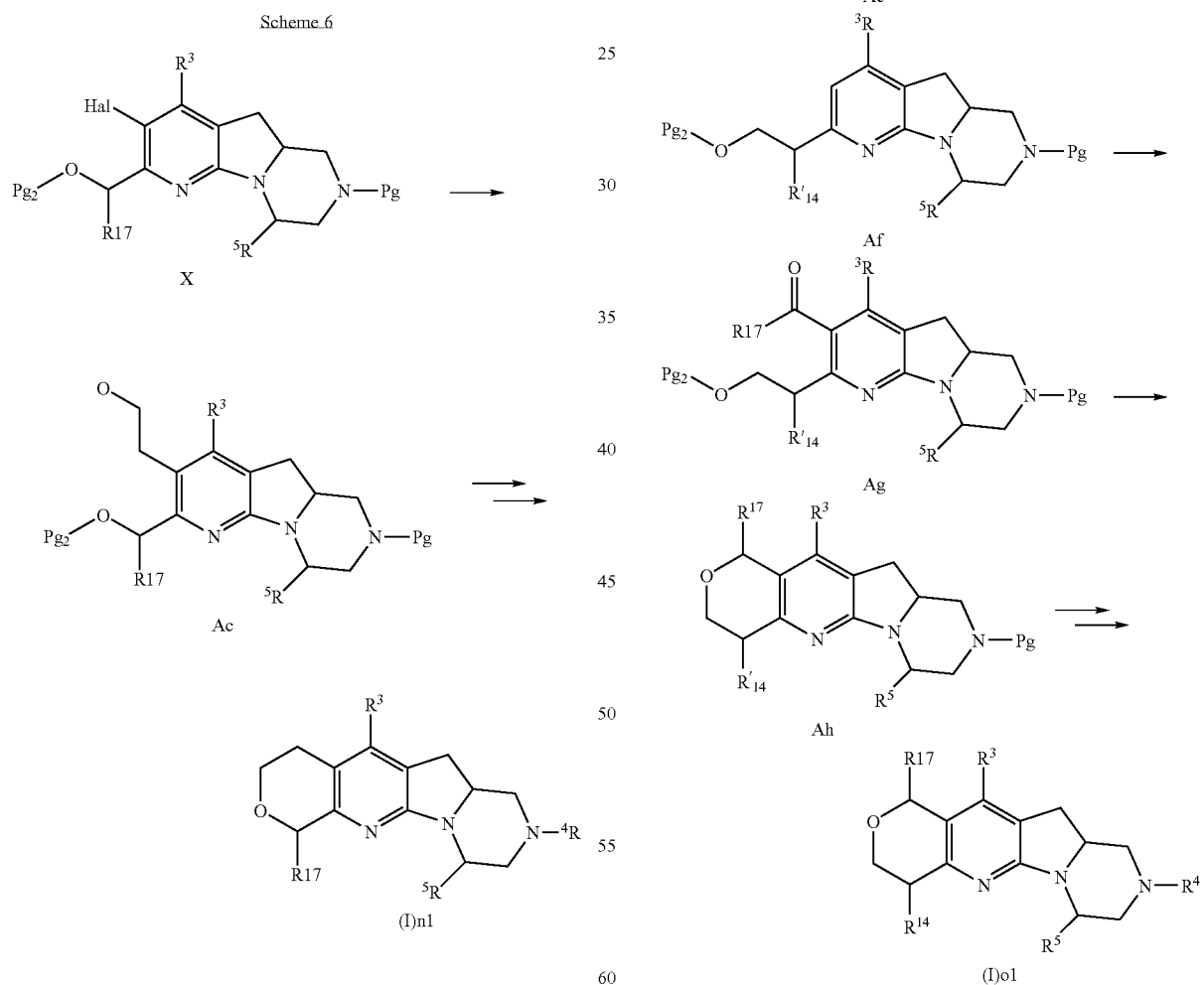

A compound of the general formula X can be metalated as described above and reacted with ethylene oxide in an inert solvent to yield a compound of the general formula Ac. Transformation to a compound of the general formula (I)n can be achieved in analogy to the transformations described above for conversion of compounds of the general formula Y to compounds of the general formula (I)m.

General synthesis of compounds type (I)o1 (Scheme 7)

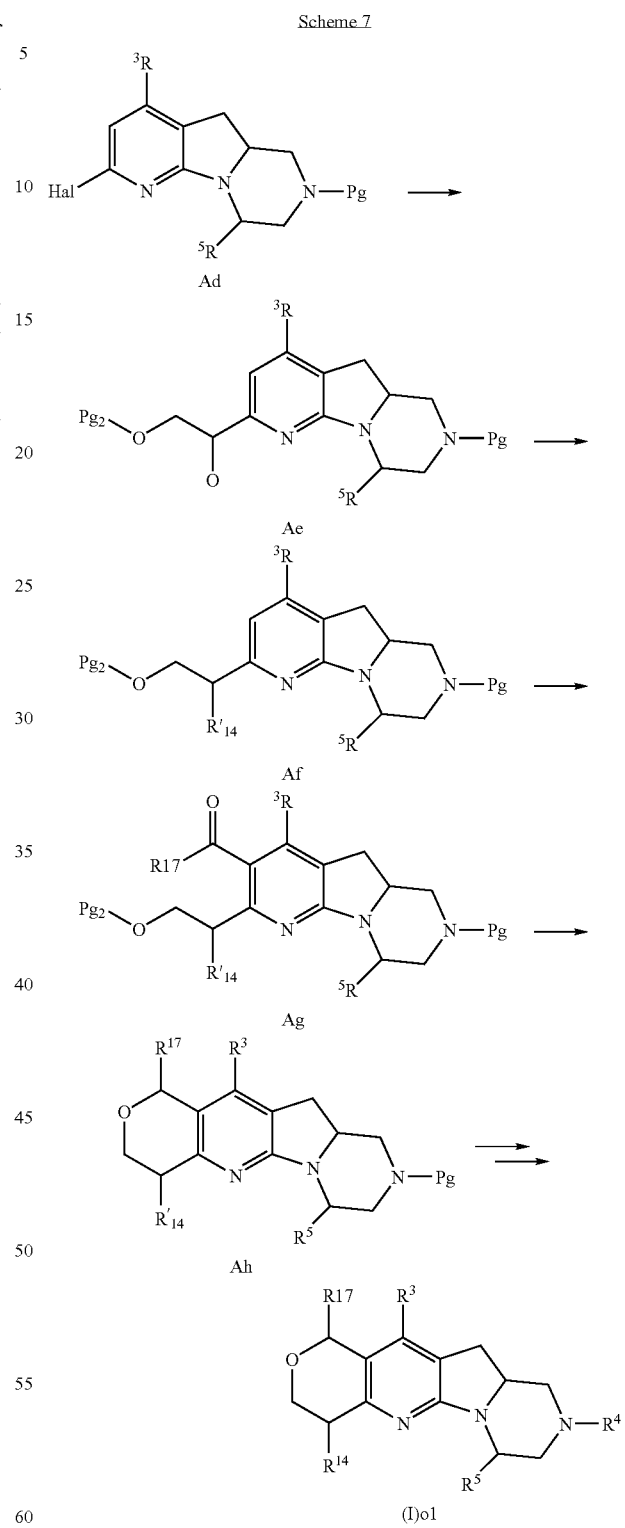

A compound of the general formula Ad can be metalated in analogy to a compound of the general formula C as described above and reacted with a protected 2-hydroxyacetaldehyde to yield a compound of the general formula Ae which can be transformed into a compound of the general formula Af in analogy to the above described transformation of a compound of the general formula Y to a compound of the general formula Z. A compound of the general formula Af can be converted to a compound of the general formula Ag in analogy to the transformation of a compound of the general formula A to a compound of the general formula D and further processed to a compound of the general formula Ah by analogy of the preparation of a compound of the general formula F from a compound of the general formula D. Transformation to compounds of the general formula (I)o1 can be achieved in analogy to the transformations described above for conversion of compounds of the general formula Y to compounds of the general formula (I)m1.

It is a further embodiment of the invention to provide compounds according to formula I for use as therapeutically active substances.

It is another embodiment of the invention to provide compounds of formula I as described above for the production of medicaments for the prophylaxis and therapy of illnesses which are caused by disorders associated with the 5-$HT_2$ receptors, the 5-$HT_{2A}$, 5-$HT_{2B}$ and 5-$HT_{2C}$ subtypes, particularly the 5-$HT_{2C}$ subtype.

Likewise it is an embodiment of the invention to provide pharmaceutical compositions comprising a compound of formula I and a therapeutically inert carrier.

It is a further embodiment of the invention to provide a compound in accordance with formula I for use in the production of medicaments for the treatment and prophylaxis of eating disorders and obesity.

Also preferred is the use of a compound in accordance with formula I for the production of medicaments for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance.

Particularly preferred is the use of a compound in accordance with formula I for the production of medicaments for the treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance.

It is a further particularly preferred embodiment of the invention to provide a compound in accordance with formula I for use in the production of medicaments for the treatment of Type II diabetes (non-insulin dependent diabetes mellitus (NIDDM)).

An embodiment of the invention is the use of compounds in accordance with formula I for the production of medicaments for the treatment and prophylaxis of disorders of the central nervous system, cardiovascular disorders, gastrointestinal disorders, diabetes insipidus and sleep apnea.

Particularly an embodiment of the invention is the above use, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggression, age-related memory disorders, chronic fatigue syndrome, drug and alcohol addiction, bulimia, anorexia nervosa, premenstrual tension, trauma, stroke, neurodegenerative diseases, encephalitis, meningitis and urinary incontinence.

A further preferred embodiment of the present invention is the above mentioned use of the compounds according to formula I, wherein the cardiovascular disorder is thrombosis.

Also preferred is the aforementioned use of the compounds according to formula I, wherein the gastrointestinal disorder is dysfunction of gastrointestinal motility.

A further embodiment of the invention are compounds in accordance with formula I, when manufactured according to the processes described herein.

A further embodiment of the present invention is a method for the treatment and prophylaxis of disorders of the central nervous system, cardiovascular disorders, gastrointestinal disorders, diabetes insipidus and sleep apnea, which method comprises administering an effective amount of a compound of formula I as described.

Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis, meningitis and urinary incontinence.

A further embodiment of the present invention is the method for the treatment and prophylaxis of sexual dysfunction which method comprises administering an effective amount of a compound of formula I as described.

Preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), diabetes insipidus, hyperglycemia, diabetic complications and insulin resistance, which method comprises administering an effective amount of a compound in accordance with formula I.

Particularly preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), hyperglycemia, diabetic complications and insulin resistance, which method comprises administering an effective amount of a compound in accordance with formula I.

It is a preferred embodiment of the invention to provide a method for the treatment and prophylaxis of eating disorders and obesity, which method comprises administering an effective amount of a compound of formula I.

It is a preferred embodiment of the invention to provide a method for the treatment and prophylaxis of Type II diabetes (non-insulin dependent diabetes mellitus (NIDDM), which method comprises administering an effective amount of a compound of formula I.

It is a further preferred embodiment of the invention to provide a method of treatment of obesity in a human which comprises administration of a therapeutically effective amount of a compound according to formula I and a therapeutically effective amount of a lipase inhibitor, particularly, wherein the lipase inhibitor is orlistat. Also an embodiment of the invention is the method as described above for the simultaneous, separate or sequential administration.

It is a further preferred embodiment to provide a method of treatment of Type II diabetes (non-insulin dependent diabetes mellitus (NIDDM) in a human which comprises administration of a therapeutically effective amount of a compound according to formula I and a therapeutically effective amount of a lipase inhibitor, particularly, wherein the lipase inhibitor is orlistat. Also an embodiment of the invention is the method as described above for the simultaneous, separate or sequential administration of a compound according to formula I and a lipase inhibitor, particularly orlistat.

It is a further preferred embodiment of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an embodiment of the invention to provide a method as described above for the simultaneous, separate or sequential administration of a compound according to formula I and a lipase inhibitor, particularly orlistat.

It is a further particularly preferred embodiment of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an embodiment of the invention to provide a method as described above for the simultaneous, separate or sequential administration of a compound according to formula I and a lipase inhibitor, particularly orlistat.

A further embodiment of the invention is the use of a compound of formula I in the manufacture of a medicament for the treatment and prevention of obesity in a patient who is also receiving treatment with a lipase inhibitor and particularly, wherein the lipase inhibitor is orlistat.

A further embodiment of the invention is the use of a compound of formula I in the manufacture of a medicament for the treatment and prevention of obesity in a patient who is also receiving treatment with a compound selected from the following list: Nerve growth factor agonist (e.g. axokine), growth hormone agonist (e.g. AOD-9604), adrenergic uptake inhibitor (e.g. GW-320659), 5-HT reuptake inhibitor (e.g. Prozac), 5-HT/NA reuptake inhibitor (e.g. sibutramine), DA reuptake inhibitor (e.g. Buproprion), 5-HT, NA and DA reuptake blocker, steroidal plant extract (eg P57), NPY1 or 5 antagonist, MC4 agonist, CCKA agonist, MCH antagonist (e.g. SNAP 7941), H3 receptor antagonist, H1 agonist, CRF agonist, Galanin antagonist, uncoupling protein, orexin antagonist, GLP-1 agonist, IL-6 agonist, α-MSH agonist, AGRP antagonist, 5-HT$_{1B}$ agonist, POMC antagonist, NN2211, Exendin-4 agonists and CB-1 inverse agonist or antagonist.

A further embodiment of the invention is the use of a compound of formula I in the manufacture of a medicament for the treatment and prevention of Type II diabetes (non-insulin dependent diabetes mellitus (NIDDM)) in a patient who is also receiving treatment with a lipase inhibitor and particularly, wherein the lipase inhibitor is orlistat.

A further preferred embodiment of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance in a patient who is also receiving treatment with a lipase inhibitor particularly, wherein the lipase inhibitor is orlistat.

A further particularly preferred embodiment of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance in a patient who is also receiving treatment with a lipase inhibitor particularly, wherein the lipase inhibitor is orlistat.

A further embodiment of the present invention is the use of a compound according to formula I in the manufacture of a medicament for the treatment of sexual dysfunction.

It is also an embodiment of the invention to provide a pharmaceutical composition comprising a compound of formula I, a therapeutically inert carrier and a therapeutically effective amount of a lipase inhibitor, particularly, wherein the lipase inhibitor is orlistat.

Other combinations which may be considered are Sibutramine comprising combinations or combination with CB-1 inverse agonist/antagonist.

It is also a preferred embodiment of the invention to provide a method of treatment and/or prevention in mammals disorders where a reduction of the blood glucose concentration is beneficial comprising administering a therapeutically effective amount of a compound of formula I. Particularly preferred is this use or method wherein the disorders are disorders involving elevated plasma blood glucose.

The compounds of formula (I) may be used in the treatment (including prophylactic treatment) of disorders associated with 5-HT$_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

A further preferred embodiment of the present invention is a process for the preparation of a compound of formula I comprising one of the following reactions:

reacting a compound of formula

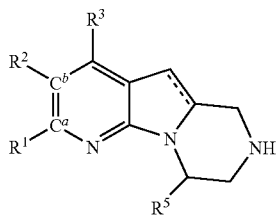

by reductive amination with aldehydes or keytones or by acylation with activated carbonic acid derivatives and reduction of the resulting amines by lithium aluminiumhydride in order to obtain a compound of formula (I)

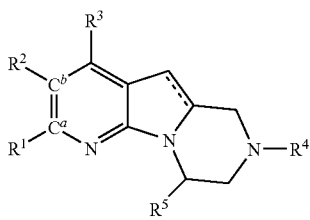
(I)

wherein $R^1$ to $R^5$ are defined as before;

reduction of a compound of formula

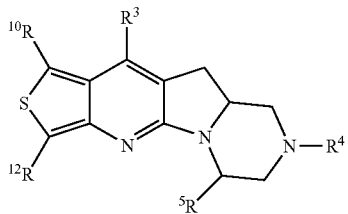

in order to obtain a compound of formula

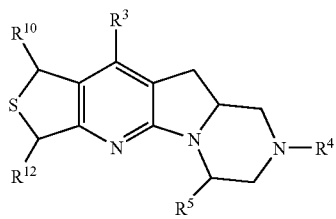

wherein $R^3$, $R^4$, $R^5$, $R^{10}$ and $R^{12}$ are defined as before. Particularly preferred is the above reaction, wherein the reduction is made after protection of the piperazine as the Boc derivative by suitable reducing agents such as silanes in particular polymethylhydroxy silane in the presence of metal catalysts such as e.g. palladium salts in particular palladium acetate and a fluoride source such as e.g. hydrofluoric acid salts, in particular potassium fluoride.

reduction of a compound of formula

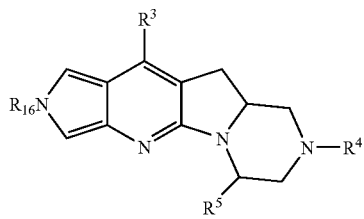

in order to obtain a compound of the formula

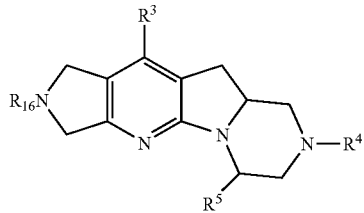

wherein $R^3$, $R^4$, $R^5$ and $R^{16}$ are defined as before. Preferred is the above process, wherein the reduction is made by hydrogenolysis in suitable solvents such as e.g. aqueous acids in particular aqueous acetic acid in the presence of a suitable catalyst for example palladium on charcoal.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g. intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g. containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g. obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

Binding to Serotonin Receptors

The binding of compounds of formula (I) to serotonin receptors was determined in vitro by standard methods. The preparations were investigated in accordance with the assays given hereinafter.

Method (a): For the binding to the 5-HT$_{2C}$ receptor the 5-HT$_{2C}$ receptors were radiolabeled with [$^3$H]-5-HT. The affinity of the compounds for 5-HT$_{2C}$ receptors in a CHO cell line was determined according to the procedure of D. Hoyer, G. Engel and H. O. Kalkman, *European J. Pharmacol.*, 1985, 118, 13-23.

Method (b): For the binding to the 5-HT$_{2B}$ receptor the 5-HT$_{2B}$ receptors were radiolabeled with [$^3$H]-5-HT. The affinity of the compounds for human 5-HT$_{2B}$ receptors in a CHO cell line was determined according to the procedure of K. Schmuck, C. Ullmer, P. Engels and H. Lubbert, *FEBS Lett.*, 1994, 342, 85-90.

Method (c): For the binding to the 5-HT$_{2A}$ receptor the 5-HT$_{2A}$ receptors were radiolabeled with [$^{125}$I]-DOI. The affinity of the compounds for 5-HT$_{2A}$ receptors in a CHO cell line was determined according to the procedure of D. J. McKenna and S. J. Peroutka, *J. Neurosci.*, 1989, 9, 3482-90.

The thus determined activity of the compound of the Example is shown in Table 1.

TABLE 1

|  | Method (a) K$_i$ (2C) | Method (b) K$_i$ (2B) | Method (c) K$_i$ (2A) |
| --- | --- | --- | --- |
| Example 17 | 23.4 nM | 759.7 nM | 634.5 nM |
| Example 19 | 5.5 nM | 26.3 nM | 80.2 nM |
| Example 33 | 5.3 nM | 21.1 nM | 98.9 nM |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

Functional Activity

The functional activity of compounds of formula (I) was assayed using a Fluorimetric Imaging Plate Reader (FLIPR). CHO cells expressing the human 5-HT$_{2C}$ or human 5-HT$_{2A}$ receptors were counted and plated into standard 96 well microtitre plates on the day before testing to give a confluent monolayer. The cells were then loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 μL of the assay buffer) was added at a rate of 70 μL/sec to each well of the FLIPR 96 well plate during fluorescence measurements. The measurements were taken at 1 sec intervals and the maximum fluorescent signal was measured (approx 10-15 secs after drug addition) and compared with the response produced by 10 μM 5-HT (defined as 100%) to which it was expressed as a percentage response (relative efficacy). Dose response curves were constructed using Graphpad Prism (Graph Software Inc.).

TABLE 2

|  | h5-HT2C | | h5-HT2A | |
| --- | --- | --- | --- | --- |
| Compound | EC$_{50}$ [nM] | Rel. Eff. [%] | EC$_{50}$ [nM] | Rel. Eff. [%] |
| Example 17 | 12.4 | 95 | 534.1 | 35 |
| Example 19 | 8.4 | 87 | >1000 | 3 |
| Example 80 | 30.8 | 89 | 212.4 | 47 |

The compounds of formula (I) have activity at the human 5-HT$_{2C}$ receptor in the range of 10,000 to 0.01 nM.

Preferred compounds of formula I as described above have activity at the human 5-HT$_{2C}$ receptor below 10000 nM; especially preferred compounds below 1000 nM, particularly preferred compounds below 100 nM. Most preferred compounds have activity at the human 5-HT$_{2C}$ receptor below 30 nM.

Regulation of Feeding Behavior

The in vivo activity of compounds of formula (1) was assessed for their ability to regulate feeding behavior by recording food consumption in food deprived animals.

Rats were trained to have access to food for 2 h per day and were food deprived for 22 h. When they were trained under this schedule, the amount of food taken every day during these 2h food intake session was consistent day after day.

To test the ability of the 5-HT$_{2c}$ receptor agonists to decrease food intake, 8 animals were used in a cross-over study. Rats were individually housed in plexiglass boxes with a grid on the floor and a paper was placed below the cage floor to collect any spillage. A food dispenser (becher) filled with a preweighed amount of food was presented to them for 2 h. At the end of the food intake session, rats returned to their home cage. Each rat was weighed before the start of the experiment and the amount of food consumed during this 2 h food intake session was recorded. Either various doses of test compound or Vehicle was administered orally 60 min before the 2 h food intake session. Sibutramine was included in the experiment as a positive control.

An Anova analysis with repeated measures was used followed by a posthoc test Student Neumann-Keuls. *P<0.05 compared to Saline-treated rats.

The minimum effective dose (m.e.d.) is defined as the lowest dose which produces a statistically significant reduction in food intake. The minimum effective doses for selected particularly preferred compounds of formula I are 30 mg/kg p.o. and below.

EXAMPLES

Example 1

(5R,8aR)-5-Methyl-1,3,5,6,7,8,8a,9-octahydro-2-oxa-4,4b,7-triaza-cyclopenta[b]fluorene dihydrogenphosphate A mixture of 22.7g (0.046 mol) (4R,9aR)-6-[dimethyl-(1,1,2-trimethyl-propyl)-silanyloxymethyl]-7-formyl-4-methyl-3,4,9,9a-tetrahydro-1H-2,4a,5-triaza-fluorene-2-carboxylic acid tert-butyl ester and 22.7 g ammonium fluoride (0.61 mol) in 500 ml methanol was heated to reflux for 1 h. The reaction mixture cooled to room temperature and partitioned between water and ethyl acetate. The phases were separated and the organic phase was washed with water and brine dried over sodium sulfate filtered and evaporated. The residue was taken up in 230 ml of dichloromethane and cooled to 0° C. To the resulting solution was added 23 ml triethylsilane and 113 ml trifluoroacetic acid and the mixture was stirred with thawing to room temperature for 17 h. The resulting orange red solution was evaporated under aspirator vacuum. The residue was partitioned between 200 ml water and 200 ml ethyl acetate. The phases were separated and the organic phase was extracted twice with 100 ml water. The combined aqueous phases were mixed with 300 ml dichloromethane and the pH of the mixture was adjusted to 12.00 by addition of a 28% solution of sodium hydroxide in water. The phases were separated and the aqueous phase was extracted two more times with 100 ml dichloromethane. The combined dichloromethane phases were dried over sodium sulfate evaporated to dryness and purified by chromatography on silica gel with dichloromethane:methanol:25% aqueous ammonia=90:10:1 to yield 8.11 g (76%) of (5R,8aR)-5-methyl-1,3,5,6,7,8,8a,9-octahydro-2-oxa-4,4b,7-triaza-cyclopenta[b]fluorene as yellow orange foam. (MS: 232 (M+H$^+$))

This material was taken up in 150 ml methanol. To the resulting solution was added drop wise during 10 minutes a solution of 3.436 g ortho phosphoric acid in 85 ml methanol. The mixture was stirred at room temperature for 1 h and at 0° C. for 2 h. The precipitate was collected by filtration washed with 70 ml ice cold methanol and dried to constant weight under aspirator vacuum to yield 9.125 g (79.6%) white crystals of the title compound as the dihydrogen phosphate salt. Upon concentration of the mother liquor a second crop of 1.06 g (9.2%) slightly yellow crystals can be obtained. (Elemental analysis calculated C, 47.42; H, 6.12 N, 12.76 found C, 47.28; H, 5.99 N, 12.72)

The starting material (4R,9aR)-6-[dimethyl-(1,1,2-trimethyl-propyl)-silanyloxymethyl]-7-formyl-4-methyl-3,4,9,9a-tetrahydro-1H-2,4a,5-triaza-fluorene-2-carboxylic acid tert-butyl ester was obtained by the following sequence of steps starting from known precursors.

Step 1: (4R,9aR)-6-[Dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester To a solution of 16.1 g (0.0504 mol) (4R,9aR)-6-Hydroxymethyl-4-methyl-3,4,9,9a-tetrahydro-1H-2,4a,5-triaza-fluorene-2-carboxylic acid tert-butyl ester in 100 ml dimethylformamide was added 6.86g (0.100 mol) imidazole and 11.9 ml (0.0505 mol) thexyldimethylchlorosilane and the mixture was stirred at room temperature for 20 h. The reaction mixture was partitioned between ethyl acetate and 250 ml of a 10% aqueous solution of citric acid. The phases were separated and the organic phase was washed once with 250 ml of a 10% aqueous solution of citric acid twice with 250 ml water once with 250 ml of a saturated aqueous solution of sodium bicarbonate and once with brine dried over sodium sulfate filtered and evaporated to dryness and purified by chromatography on silica gel with dichloromethane and a mixture of dichloromethane and ethyl acetate=9:1 to yield 22.78 g (97.9%) of the title compound as colorless oil (MS: 462 (M+H$^+$)).

Step 2: (4R,9aR)-7-Bromo-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester To a solution of 22.78 g (4R,9aR)-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester in 200 ml tetrahydrofuran was added at 0° C. 8.78 g (0.049 mol) N-bromosuccinimide and the mixture was stirred at 0° C. for 30 minutes. The reaction mixture was diluted with 500 ml ethyl acetate and extracted sequentially with a 10% aqueous solution of sodium thiosulfate, a 10% aqueous solution of citric acid, water and brine dried over sodium sulfate, evaporated under aspirator vacuum and dried to constant weight under high vacuum to yield 26.5 g of the title compound as colorless oil. (MS: 541 (M+H$^+$)).

Step 3 (4R,9aR)-6-[Dimethyl-(1,1,2-trimethyl-propyl)-silanyloxymethyl]-7-formyl-4-methyl-3,4,9,9a-tetrahydro-1H-2,4a,5-triaza-fluorene-2-carboxylic acid tert-butyl ester To a solution of 26.5 g (0.049 mol) (4R,9aR)-7-bromo-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester in 800 ml toluene was added at −78° C. during 10 minutes 50 ml of a 1.5 M solution of tert. butyllithium in pentane. The reaction mixture was stirred at −78° C. for 30 minutes. To the resulting orange solution was added 30 ml dimethylformamide during 3 minutes. The reaction mixture was stirred at −78° C. for 30 minutes and the cooling bath was then removed and the mixture was stirred for 30 min at ambient temperature. The reaction was quenched by addition of 300 ml of a 10% aqueous solution of citric acid and extracted with ethyl acetate. The organic phase was washed with a 10% aqueous solution of sodium bicarbonate and brine, dried over sodium sulfate, evaporated under aspirator vacuum and purified by chromatography on silica gel with heptane:ethyl acetate=4:1 to 3:1. to yield 22.70 g (94.6%) of the title compound as yellow foam (MS: 490 (M+H$^+$)).

Example 2

(5R,8aS)-5-Methyl-1,3,5,6,7,8,8a,9-octahydro-2-oxa-4,4b,7-triaza-cyclopenta[b]fluorene Starting from (4R,9aS)-6-hydroxymethyl-4-methyl-3,4,9,9a-tetrahydro-1H-2,4a,5-triaza-fluorene-2-carboxylic acid tert-butyl ester the title compound was obtained by an analogous sequence of steps as in example 1 as colorless foam. MS: 232.1 (M+H$^+$)

Example 3

(R)-5-Methyl-1,3,5,6,7,8-hexahydro-2-oxa-4,4b,7-triaza-cyclopenta[b]fluorene

To a solution of 0.050 g (5R,8aR)-5-methyl-3,5,6,8,8a,9-hexahydro-1H-2-oxa-4,4b,7-triaza-cyclopenta[b]fluorene-7-carboxylic acid tert-butyl ester in 3 ml dichloromethane was added in 4 portions in intervals of 30 min 0.20 g manganese dioxide. The mixture was then stirred at room temperature for 18 h. The product was purified by chromatography on silica gel with heptane:ethyl acetate=1:1. to yield a yellow oil which was taken up in 1 ml trifluoroacetic acid and kept at room temperature for 30 min. The solvent was evaporated and the residue partitioned between water and ethyl acetate. The phases were separated and the aqueous phase was neutralized to pH 12 by addition of 2N sodium hydroxide and extracted with dichloromethane. The dichloromethane phase was washed with half concentrated brine and purified by chromatography on silca gel with dichloromethane:methanol:ammonia=90:10:0.1. to yield 0.011 g of the title compound as slightly yellow oil. (MS 232.1 (M+H$^+$))

The Starting Material was Obtained in the Following Manner.

To a solution of 0.200 g (5R,8aR)-5-methyl-1,3,5,6,7,8,8a,9-octahydro-2-oxa-4,4b,7-triaza-cyclopenta[b]fluorene in 2 ml dichloromethane was added 0.200 di tert.butyldicarbonate and the mixture was kept at room temperature for 1 h. The solvent was evaporated and the residue was purified by chromatography on silica gel with heptane:ethyl acetate=2:1. to yield 0.22 g (5R,8aR)-5-methyl-3,5,6,8,8a,9-hexahydro-1H-2-oxa-4,4b,7-triaza-cyclopenta[b]fluorene-7-carboxylic acid tert-butyl ester as a colorless solid (MS: 332.4 (M+H$^+$))

Alternatively the starting material can be obtained from (4R,9aR)-6-[dimethyl-(1,1,2-trimethyl-propyl)-silanyloxymethyl]-7-formyl-4-methyl-3,4,9,9a-tetrahydro-1H-2,4a,5-triaza-fluorene-2-carboxylic acid tert-butyl ester in analogy to example 9b.

Example 4

5-Methyl-1,3,5,6,7,8,8a,9-octahydro-2-oxa-4,4b,7-triaza-cyclopenta[b]fluorene

Starting from (4S,9aR)-6-hydroxymethyl-4-methyl-3,4,9,9a-tetrahydro-1H-2,4a,5-triaza-fluorene-2-carboxylic acid tert-butyl ester the title compound was obtained by an analogous sequence of steps as in example 1 as a colorless foam (MS: 232.4 (M+H$^+$)).

Example 5

(5R,8aR)-5,7-Dimethyl-1,3,5,6,7,8,8a,9-octahydro-2-oxa-4,4b,7-triaza-cyclopenta[b]fluorene A mixture of 0.100 g (5R,8aR)-5-methyl-3,5,6,8,8a,9-hexahydro-1H-2-oxa-4,4b,7-triaza-cyclopenta[b]fluorene-7-carboxylic acid tert-butyl ester and 0.040 g lithium aluminum hydride in 3 ml tetrahydrofuran was heated to reflux for 2 h. The reaction mixture was cooled to room temperature and partitioned between water and ethyl acetate. The organic phase was washed with brine evaporated and purified by chromatography on silica gel with dichloromethane:methanol:ammonia=90:10:1. to yield 0.053 g of the title compound as slightly yellow gum (MS: 246.4 (M+H$^+$))

Example 6

(5R,8aR)-7-Ethyl-5-methyl-1,3,5,6,7,8,8a,9-octahydro-2-oxa-4,4b,7-triaza-cyclopenta[b]fluorene Starting from 1-((5R,8aR)-5-methyl-3,5,6,8,8a,9-hexahydro-1H-2-oxa-4,4b,7-triaza-cyclopenta[b]fluoren-7-yl)-ethanone by the same procedure as in example 5 the title compound was obtained as slightly yellow gum (MS: 260.3 (M+H$^+$))

Example 7

1-((5R,8aR)-5-Methyl-3,5,6,8,8a,9-hexahydro-1H-2-oxa-4,4b,7-triaza-cyclopenta[b] fluoren-7-yl)-ethanone To a solution of 0.33 (5R,8aR)-5-Methyl-1,3,5,6,7,8,8a,9-octahydro-2-oxa-4,4b,7-triaza-cyclopenta[b]fluorene dihydrogenphosphate in 4 ml water was added a solution of 1.3 ml acetic acid anhydride in 4 ml dichloromethane and the pH of the mixture was adjusted to 12.00 by addition of 1N aqueous sodium hydroxide. The mixture was stirred at room temperature for 15 minutes. The phases were separated and the organic phase was washed with 10% aqueous citric acid, saturated aqueous sodium bicarbonate and brine dried over sodium sulfate and evaporated to dryness to yield 0.25 g of the title compound as slightly yellow oil (MS: 274.1 (M+H$^+$)).

Example 8

(5R,8aR)-3,5-Dimethyl-1,3,5,6,7,8,8a,9-octahydro-2-oxa-4,4b,7-triaza-cyclopenta[b]fluorene Starting from (4R,9aR)-6-{(S)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester or (4R,9aR)-6-{(RS)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester The title compound was obtained in analogy to example 1 in 77% yield as slightly yellow gum (MS: 246.3 (M+H$^+$)) as a 2:1 mixture of epimers.

The starting material (4R,9aR)-6-{(RS)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester was obtained by the following sequence of steps.

Step 1 (4R,9aR)-6-Formyl-4-methyl-3,4,9,9a-tetrahydro-1H-2,4a,5-triaza-fluorene-2-carboxylic acid tert-butyl ester To a solution of 2.00 g (4R,9aR)-6-Hydroxymethyl-4-methyl-3,4,9,9a-tetrahydro-1H-2,4a,5-triaza-fluorene-2-carboxylic acid tert-butyl ester in 20 ml dichloromethane was added 6.00 g manganese dioxide in 3 portions of 2.00 g in intervals of 1 h at room temperature while stirring. The reaction mixture was stirred for 2 more hours at room temperature. The solids were removed by filtration over dicalite and the mother liquor was evaporated and the residue was purified by chromatography on silica gel with heptane:ethyl acetate=1:1 to yield 1.600 g of the title compound as slightly yellow crystals (MS: 316.0 (M+H$^+$))

Step 2: (4R,9aR)-6-(1-(RS)-Hydroxy-ethyl)-4-methyl-3,4,9,9a-tetrahydro-1H-2,4a,5-triaza-fluorene-2-carboxylic acid tert-butyl ester To a solution of 10.00 g (4R,9aR)-6-Formyl-4-methyl-3,4,9,9a-tetrahydro-1H-2,4a,5-triaza-fluorene-2-carboxylic acid tert-butyl ester in 100 ml tetrahydrofuran was added dropwise at 0° C. 20 ml of a ca 3M solution of methyl magnesium bromide solution in ether. The mixture was stirred at 0° C. for 30 min. The reaction mixture was quenched with 10% aqueous ammonium chloride and extracted with ethyl acetate. The organic phase was washed with 105 aqueous citric acid, 10% aqueous sodium bicarbonate and brine, dried over sodium sulfate, evaporated and dried to constant weight under high vacuum to yield 10.0 g of the title compound as colorless oil (MS: 334.5 (M+H$^+$)).

Step 3 (4R,9aR)-6-{(RS)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester By applying the same sequence of reactions as in example 1 (step 1 to step 3) (4R,9aR)-6-(1-(RS)-hydroxy-ethyl)-4-methyl-3,4,9,9a-tetrahydro-1H-2,4a,5-triaza-fluorene-2-carboxylic acid tert-butyl ester was converted to the title compound (4R,9aR)-6-{(RS)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester which was obtained as colorless oil (MS: 504.5 (M+H$^+$)).

Example 9

(3S,5R,8aR)-3,5-Dimethyl-1,3,5,6,7,8,8a,9-octahydro-2-oxa-4,4b,7-triaza-cyclopenta[b]fluorene Starting from the product of example 8 the title compound was obtained by preparative chiral HPLC on a Chiralpak AD column using ethanol heptane mixtures as eluent as slightly yellow crystals m.p.: 90-91° C.

Alternatively (3S,5R,8aR)-3,5-dimethyl-1,3,5,6,7,8,8a,9-octahydro-2-oxa-4,4b,7-triaza-cyclopenta[b]fluorene and (3R,5R,8aR)-3,5-dimethyl-1,3,5,6,7,8,8a,9-octahydro-2-oxa-4,4b,7-triaza-cyclopenta[b]fluorene dihydrogenphosphate could by obtained from (4R,9aR)-6-{(S)-1-[dimethyl-(1,1,2-trimethyl-propyl)-silanyloxy]-ethyl}-7-formyl-4-methyl-3,4,9,9a-tetrahydro-1H-2,4a,5-triaza-fluorene-2-carboxylic acid tert-butyl ester by the following sequence of reactions.

Step 1:(3S,5R,8aR)-3,5-Dimethyl-3,5,6,8,8a,9-hexahydro-1H-2-oxa-4,4b,7-triaza-cyclopenta[b]fluorene-7-carboxylic acid tert-butyl ester A mixture of 1.008 g (4R,9aR)-6-{(S)-1-[dimethyl-(1,1,2-trimethyl-propyl)-silanyloxy]-ethyl}-7-formyl-4-methyl-3, 4,9,9a-tetrahydro-1H-2,4a,5-triaza-fluorene-2-carboxylic acid tert-butyl ester and 0.0889 g ammonium fluoride in 10 ml methanol was heated to reflux for 22 h. The mixture was cooled to room temperature and 0.228 g sodium cyanoborohydride was added. The mixture was cooled to 0° C. and 2.00 ml glacial acetic acid was added during 5 min. The mixture was stirred at 0° C. for 30 min. The reaction mixture was partitioned between water and ethyl acetate. The phases were separated and the organic phase was washed twice with 10% aqueous sodium bicarbonate and brine dried over sodium sulfate and evaporated to yield 0.77 g yellow brownish crystals which were purified by chromatography on silica gel with heptane:ethyl acetate=2:1. to yield 0.587 g (3S,5R,8aR)-3,5-dimethyl-3,5,6,8,8a,9-hexahydro-1H-2-oxa-4,4b,7-triaza-cyclopenta[b]fluorene-7-carboxylic acid tert-butyl ester as white crystals m.p.:143-144° C.

Step 2

The product of step 1 was treated with trifluoroacetic acid at 0° C. for 30 minutes. The mixture was evaporated under aspirator vacuum and the residue was partitioned between water and ethyl acetate. The phases were separated and the aqueous phase was mixed with dichloromethane. The pH of this mixture was adjusted to 12.00 by addition of 28% aqueous sodium hydroxide. The phases were separated and the organic phase was washed with half concentrated brine dried over sodium sulfate and evaporated. The residue was purified by chromatography on silica gel with methylenechloride:methanol:ammonia=90:10:1 to yield the title compound (3S,5R,8aR)-3,5-Dimethyl-1,3,5,6,7,8,8a,9-octahydro-2-oxa-4,4b,7-triaza-cyclopenta[b]fluorene as slightly yellow crystals m.p.: 90-91° C.

Step 3

To a solution of 6.70 g (0.0273 mol) (3R,5R,8aR)-3,5-Dimethyl-1,3,5,6,7,8,8a,9-octahydro-2-oxa-4,4b,7-triaza-cyclopenta[b]fluorene in 90 ml methanol was added a solution of 2.67 g (0.0273 mol) ortho phosphoric acid in 30 ml methanol and the mixture was stirred at room temperature for 1 h. The solvent was evaporated and the residue was taken up in 130 ml ethanol. To the mixture were added seed crystals and stirring was continued for 22 h. The solids were collected by filtration and dried to constant weight under high vacuum to yield 8.74 g (3R,5R,8aR)-3,5-dimethyl-1,3,5,6,7,8,8a,9-octahydro-2-oxa-4,4b,7-triaza-cyclopenta[b]fluorene dihydrogenphosphate as white crystals. (elemental analysis calculated C, 48.83H, 6.47 N, 12.20 found C, 48.77H, 6.38 N, 12.08)

Example 10

(3R,5R,8aR)-3,5-Dimethyl-1,3,5,6,7,8,8a,9-octahydro-2-oxa-4,4b,7-triaza-cyclopenta[b]fluorene Starting from the product of example 8 the title compound was obtained by preparative chiral HPLC on a Chiralpak AD column using ethanol heptane mixtures as eluent as slightly yellow crystals m.p.: 78-79° C.

Example 11

(3S,5R,8aR)-3-Ethyl-5-methyl-1,3,5,6,7,8,8a,9-octahydro-2-oxa-4,4b,7-triaza-cyclopenta[b]fluorene The title compound was obtained by the same sequence of reaction s as in example 8 starting from (4R,9aR)-6-Formyl- 4-methyl-3,4,9,9a-tetrahydro-1H-2,4a,5-triaza-fluorene-2-carboxylic acid tert-butyl ester and using ethyl magnesium bromide instead of methyl magnesium bromide. The title compound was isolated as the minor epimer by chiral HPLC on a Chiralpak AD column using ethanol heptane mixtures as eluent as slightly yellow oil (MS: 260.0 (M+H$^+$)) The stereochemistry was confirmed by X-ray single crystal structure determination.

Example 12

(3R,5R,8aR)-3-Ethyl-5-methyl-1,3,5,6,7,8,8a,9-octahydro-2-oxa-4,4b,7-triaza-cyclopenta[b]fluorene The tile compound was obtained by the same sequence of reaction s as in example 8 starting from (4R,9aR)-6-Formyl-4-methyl-3,4,9,9a-tetrahydro-1H-2,4a,5-triaza-fluorene-2-carboxylic acid tert-butyl ester and using ethyl magnesium bromide instead of methyl magnesium bromide. The title compound was isolated as the mayor epimer by chiral HPLC on a Chiralpak AD column using ethanol heptane mixtures as eluent as slightly yellow oil (MS: 260.3 (M+H$^+$))

Example 13

(3S,5R,8aR)-5-Methyl-3-propyl-1,3,5,6,7,8,8a,9-octahydro-2-oxa-4,4b,7-triaza-cyclopenta[b]fluorene The title compound was obtained by the same sequence of reactions as in example 8 starting from (4R,9aR)-6-Formyl-4-methyl-3,4,9,9a-tetrahydro-1H-2,4a,5-triaza-fluorene-2-carboxylic acid tert-butyl ester and using n-propyl magnesium bromide instead of methyl magnesium bromide. The title compound was isolated as the mayor epimer by chiral HPLC on a Chiralpak AD column using ethanol heptane mixtures as eluent as slightly yellow oil (MS: 274.1 (M+H$^+$))

Example 14

(3R,5R,8aR)-5-Methyl-3-propyl-1,3,5,6,7,8,8a,9-octahydro-2-oxa-4,4b,7-triaza-cyclopenta[b]fluorene The title compound was obtained by the same sequence of reaction s as in example 8 starting from (4R,9aR)-6-Formyl-4-methyl-3,4,9,9a-tetrahydro-1H-2,4a,5-triaza-fluorene-2-carboxylic acid tert-butyl ester and using n-propyl magnesium bromide instead of methyl magnesium bromide. The title compound was isolated as the minor epimer by chiral HPLC on a Chiralpak AD column using ethanol heptane mixtures as eluent as slightly yellow oil (MS: 274.1 (M+H$^+$)) The stereochemistry was confirmed by X-ray single crystal structure determination.

Example 15

(3S,5R,8aR)-3-Isopropyl-5-methyl-1,3,5,6,7,8,8a,9-octahydro-2-oxa-4,4b,7-triaza-cyclopenta[b]fluorene The title compound was obtained by the same sequence of reaction s as in example 8 starting from (4R,9aR)-6-Formyl-4-methyl-3,4,9,9a-tetrahydro-1H-2,4a,5-triaza-fluorene-2-carboxylic acid tert-butyl ester and using iso-propyl magnesium bromide instead of methyl magnesium bromide. The title compound was isolated as the mayor epimer by chiral HPLC on a Chiralpak AD column using isopropanol heptane mixtures as eluent as slightly yellow oil (MS: 274.3 (M+H$^+$))

Example 16

(3R,5R,8aR)-3-Isopropyl-5-methyl-1,3,5,6,7,8,8a,9-octahydro-2-oxa-4,4b,7-triaza-cyclopenta[b]fluorene The title compound was obtained by the same sequence of reactions as in example 8 starting from (4R,9aR)-6-Formyl-4-methyl-3,4,9,9a-tetrahydro-1H-2,4a,5-triaza-fluorene-2-carboxylic acid tert-butyl ester and using i-propyl magnesium bromide instead of methyl magnesium bromide. The title compound was isolated as the minor epimer by chiral HPLC on a Chiralpak AD column using isopropanol heptane mixtures as eluent as slightly yellow oil (MS: 274.1 (M+H$^+$))

Example 17

(3S,5R,8aR)-3-Cyclopropyl-5-methyl-1,3,5,6,7,8,8a,9-octahydro-2-oxa-4,4b,7-triaza-cyclopehta[b]fluorene The title compound was obtained by the same sequence of reaction s as in example 8 starting from (4R,9aR)-6-Formyl-4-methyl-3,4,9,9a-tetrahydro-1H-2,4a,5-triaza-fluorene-2-carboxylic acid tert-butyl ester and using cyclopropyl magnesium bromide instead of methyl magnesium bromide. The title compound was isolated as the mayor epimer by chiral HPLC on a Chiralpak AD column using ethanol heptane mixtures as eluent as slightly yellow oil (MS: 272.3 (M+H$^+$))

Example 18

(3R,5R,8aR)-3-Cyclopropyl-5-methyl-1,3,5,6,7,8,8a,9-octahydro-2-oxa-4,4b,7-triaza-cyclopenta[b]fluorene The title compound was obtained by the same sequence of reaction s as in example 8 starting from (4R,9aR)-6-Formyl-4-methyl-3,4,9,9a-tetrahydro-1H-2,4a,5-triaza-fluorene-2-carboxylic acid tert-butyl ester and using cyclopropyl magnesium bromide instead of methyl magnesium bromide. The title compound was isolated as the minor epimer by chiral HPLC on a Chiralpak AD column using ethanol heptane mixtures as eluent as slightly yellow oil (MS: 272.3 (M+H$^+$))

Example 19

(5R,8aR)-3,3,5-Trimethyl-1,3,5,6,7,8,8a,9-octahydro-2-oxa-4,4b,7-triaza-cyclopenta[b]fluorene The title compound was obtained in analogy to example 1 from (4R,9aR)-4-methyl-6-(1-methyl-1-trimethylsilanyloxy-ethyl)-3,4,9,9a-tetrahydro-1H-2,4a,5-triaza-fluorene-2-carboxylic acid tert-butyl ester.

The starting material (4R,9aR)-4-methyl-6-(1-methyl-1-trimethylsilanyloxy-ethyl)-3,4,9,9a-tetrahydro-1H-2,4a,5-triaza-fluorene-2-carboxylic acid tert-butyl ester was obtained from (4R,9aR)-4-methyl-3,4,9,9a-tetrahydro-1H-2,4a,5-triaza-fluorene-2,6-dicarboxylic acid 2-tert-butyl ester 6-methyl ester by the following procedure Step 1: (4R,9aR)-4-Methyl-6-(1-methyl-1-trimethylsilanyloxy-ethyl)-3,4,9,9a-tetrahydro-1H-2,4a,5-triaza-fluorene-2-carboxylic acid tert-butyl ester To a solution of 1.6 g (4R,9aR)-4-methyl-6-(1-methyl-1-trimethylsilanyloxy-ethyl)-3,4,9,9a-tetrahydro-1H-2,4a,5-triaza-fluorene-2-carboxylic acid tert-butyl ester in 20 ml tetrahydrofuran was added at 0° C. 5 ml of a 3M solution of methylmagnesium bromide in diethylether and the mixture was stirred at 0° C. for 30 min. The reaction mixture was partitioned between 10% aqueous ammonium chloride and ethyl acetate. The phases were separated and the organic phase was washed with 10% aqueous sodium bicarbonate and brine and evaporated. The residue was taken up in 10 ml dimethylformamide and 1.00 g imidazole and 2.00 ml trimethylchlorosilane was added and the mixture was stirred at room temperature for 2 h. The reaction mixture was partitioned between dichloromethane and 10% aqueous citric acid. The phases were separated and the organic phase was washed with 10% aqueous sodium bicarbonate and brine, dried over magnesium sulfate, evaporated and dried under high vacuum to constant weight to yield 1.800 g of the title compound as slightly yellow oil. (MS: 420.4 (M+H$^+$))

Example 20

(5R,8aR)-1,5-Dimethyl-1,3,5,6,7,8,8a,9-octahydro-2-oxa-4,4b,7-triaza-cyclopenta[b]fluorene The title compound was obtained in analogy to example 1 by using dimethylacetamide instead of dimethylformamide in Step 3 as slightly yellow oil. (MS: 246.1 (M+H$^+$))

Example 21

(5R,8aR)-1,1,5-Trimethyl-1,3,5,6,7,8,8a,9-octahydro-2-oxa-4,4b,7-triaza-cyclopenta[b]fluorene To a solution of 0.345 g (5R,8aR)-5-methyl-1-oxo-3,5,6,8,8a,9-hexahydro-1H-2-oxa-4,4b,7-triaza-cyclopenta[b]fluorene-7-carboxylic acid tert-butyl ester in 5 ml tetrahydrofuran was added at 0° C. 2.00 ml of a 2M solution of methylmagnesium bromide in diethyl ether. The mixture was stirred at 0° C. for 30 min and at room temperature for 1 h. The reaction mixture was partitioned between 10% aqueous ammonium chloride and ethyl acetate, the phases were separated and the organic phase was washed with 10% aqueous citric acid 10% aqueous sodium bicarbonate and brine dried over sodium sulfate and evaporated. The residue was taken up in 5 ml trifluoroacetic acid and kept at room temperature for 2 h. The solvent was evaporated and the residue was partitioned between water and ethyl acetate. The phases were separated and the aqueous phase was mixed with dichloromethane. The pH of the mixture was adjusted to 12.00 by addition of 2N aqueous sodium hydroxide. The phases were separated and the organic phase was washed with half concentrated brine dried over sodium sulfate and evaporated. The residue was purified by chromatography on silica gel with dichloromethane:methanol:ammonia; 90:10:1 to yield 0.18 g of the title compound as slightly yellow oil (MS: 260.2 (M+H$^+$))

The starting material (5R,8aR)-5-methyl-1-oxo-3,5,6,8,8a,9-hexahydro-1H-2-oxa-4,4b,7-triaza-cyclopenta[b]fluorene-7-carboxylic acid tert-butyl ester was obtained by the following sequence of steps.

Step 1: (4R,9aR)-7-Bromo-6-hydroxymethyl-4-methyl-3,4,9,9a-tetrahydro-1H-2,4a,5-triaza-fluorene-2-carboxylic acid tert-butyl ester To a solution of 5.00 g (4R,9aR)-6-Hydroxymethyl-4-methyl-3,4,9,9a-tetrahydro-1H-2,4a,5-triaza-fluorene-2-carboxylic acid tert-butyl ester in 50 ml tetrahydrofuran was added at 0°° C. 2.75 g N-bromosuccinimide at once and the mixture was stirred at 0° C. for 1 h. The reaction mixture was partitioned between 10% sodium thiosulfate and ethyl acetate. The phases were separated and the organic phase was washed with 10% sodium bicarbonate and brine dried over magnesium sulfate and evaporated. The residue was triturated in ca 20 ml heptane:ethyl acetate 1:3 to yield 5.75 g of the title compound as white crystals melting at 110-112° C.

Step 2: (5R,8aR)-5-Methyl-1-oxo-3,5,6,8,8a,9-hexahydro-1H-2-oxa-4,4b,7-triaza-cyclopenta[b]fluorene-7-carboxylic acid tert-butyl ester The product of step 1 was carbonylated in methanol with carbon monoxide (35 bar) at 110° C. (24 h) in the presence of palladium acetate (0.02 eq), dppp (0.025 eq) and triethylamine (3 eq). The solvent was evaporated and the residue was purified by chromatography on silica gel with ethyl acetate:heptane to yield the title compound as with crystals (MS: 346.3 (M+H$^+$))

Example 22

(5R,8aR)-1,3,5-Trimethyl-1,3,5,6,7,8,8a,9-octahydro-2-oxa-4,4b,7-triaza-cyclopenta[b]fluorene The title compound was obtained in analogy to example 8 by using dimethylacetamide instead of dimethylformamide for quenching the pyridyl lithium intermediate. The compound was obtained as slightly yellow oil. (MS: 260.1 (M+H$^+$))

Example 23

(5R,8aR)-1, 1,3,3,5-Pentamethyl-1,3,5,6,7,8,8a,9-octahydro-2-oxa-4,4b,7-triaza-cyclopenta[b]fluorene The title compound was obtained from (4R,9aR)-6,7-bis-(1-hydroxy-1-methyl-ethyl)-4-methyl-3,4,9,9a-tetrahydro-1H-2,4a,5-triaza-fluorene-2-carboxylic acid tert-butyl ester in analogy to example 21 as slightly yellow oil starting from (MS: 288.2 (M+H$^+$))

The starting material was obtained from (4R,9aR)-6-chloro-4-methyl-3,4,9,9a-tetrahydro-1H-2,4a,5-triaza-fluorene-2-carboxylic acid tert-butyl ester by the following sequence of steps.

Step 1: (4R,9aR)-7-Bromo-6-chloro-4-methyl-3,4,9,9a-tetrahydro-1H-2,4a,5-triaza-fluorene-2-carboxylic acid tert-butyl ester was obtained from (4R,9aR)-6-chloro-4-methyl-3,4,9,9a-tetrahydro-1H-2,4a,5-triaza-fluorene-2-carboxylic acid tert-butyl ester in analogy to example 21 step 1 as white crystals melting at 112-114° C.

Step 2: (4R,9aR)-4-Methyl-3,4,9,9a-tetrahydro-1H-2,4a,5-triaza-fluorene-2,6,7-tricarboxylic acid 2-tert-butyl ester 6,7-dimethyl ester was obtained from the product of step 1 in methanol by treatment at 110° C. with carbon monoxide (5 bar 15 h, 35 bar 22 h) in the presence of palladium acetate (0.04 eq), dppf (0.025 eq), dppp (0.025 eq) and triethylamine (3 eq). as white crystals. (MS: 406.4 (M+H$^+$))

Step 3: (4R,9aR)-6,7-bis-(1-hydroxy-1-methyl-ethyl)-4-methyl-3,4,9,9a-tetrahydro-1H-2,4a,5-triaza-fluorene-2-carboxylic acid tert-butyl ester To a solution of 0.288 g (4R,9aR)-4-Methyl-3,4,9,9a-tetrahydro-1H-2,4a,5-triaza-fluorene-2,6,7-tricarboxylic acid 2-tert-butyl ester 6,7-dimethyl ester in 3.00 ml tetrahydrofuran was added at −78° C. 2.37 ml of a 3M solution of methyl magnesium bromide in diethyl ether. The reaction mixture was stirred at −78° C. for 1 h and at room temperature for 2 h. The reaction mixture was partitioned between 105 aqueous ammonium chloride and ethyl acetate. The phases were separated and the organic phase was purified by chromatography on silica gel with heptane:ethyl acetate 0.087 g of the title compound as slightly yellow oil. (MS: 406.5 (M+H$^+$))

Example 24

(5R,8aR)-5,10-Dimethyl-1,3,5,6,7,8,8a,9-octahydro-2-oxa-4,4b,7-triaza-cyclopenta[b]fluorene The title compound was obtained as slightly yellow crystals (m.p.: 118-119° C.) in analogy to example 1 starting from (4R,9aR)-6-[dimethyl-(1,1,2-trimethyl-propyl)-silanyloxymethyl]-4,8-dimethyl-3,4,9,9a-tetrahydro-1H-2,4a,5-triaza-fluorene-2-carboxylic acid tert-butyl ester.

Example 25

(4R,11aR)-4-Methyl-1,3,4,6,8,9,11,11a-octahydro-2H-7-oxa-2,4a,5-triaza-benzo[b]fluorene A solution of 0.154 g (4R,9aR)-7-[2-(tert-Butyl-dimethyl-silanyloxy)-vinyl]-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester in and 0.154 g ammonium fluoride in 3.00 ml was heated to reflux for 4 h. The reaction mixture was partitioned between water and ethyl acetate. The phases were separated and the organic phase was washed with brine dried over sodium sulfate and evaporated. To as solution of the residue in 3.00 ml dichloromethane was added at 0° C. 0.14 ml triethylsilane and 0.14 ml trifluoroacetic acid and the mixture was stirred at 0° C. for 2 h. To the resulting solution was added 0.7 ml trifluoroacetic acid and the mixture was allowed to thaw to room temperature over 17 h. The solvent was evaporated and the residue was partitioned between water and ethyl acetate. The phases were separated and the pH of the aqueous phase was adjusted to 12.00 by addition of 2N aqueous sodium hydroxide and the product was extracted with methylenechloride and purified by chromatography on silica gel with dichloromethane:methanol:ammonia=90:10:1 to yield 0.0047 g of the title compound as slightly yellow oil. (MS: 246.3 (M+H$^+$))

The starting material (4R,9aR)-7-[2-(tert-Butyl-dimethyl-silanyloxy)-vinyl]-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester was obtained by the following sequence of steps.

Step 1: (4R,9aR)-7-[2-(tert-Butyl-dimethyl-silanyloxy)-1-hydroxy-ethyl]-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester To a solution of 0.825 g (4R,9aR)-7-Bromo-6-[dimethyl-(,1,2-trimethyl-propyl)-silanyloxymethyl]-4-methyl-3,4,9,9a-tetrahydro-1H-2,4a,5-triaza-fluorene-2-carboxylic acid tert-butyl ester in 25 ml toluene was drop wise added 1.53 ml of a 1.5 M solution of tert.-butyllithium in pentane at –78° C. and the mixture was stirred at this temperature for 1 h. This solution was then added via syringe to a solution of 0.705 g (tert-butyldimethylsilyloxy) acetaldehyde in 10 ml toluene at –78° C. The mixture was stirred at this temperature for 30 min and then quenched with 20 ml 10% aqueous ammonium chloride. The product was extracted with ethyl acetate and purified by chromatography on silica gel with heptane:ethyl acetate=4:1 to yield 0.200 g of the title compound as slightly yellow oil. (MS: 637.4 (M+H$^+$))

Step 2: (4R,9aR)-7-[2-(tert-Butyl-dimethyl-silanyloxy)-vinyl]-6-[dimethyl-(1,1,2-trimethyl-propyl) silanyloxymethyl]-4-methyl-3,4,9,9a-tetrahydro-1H-2,4a,5-triaza-fluorene-2-carboxylic acid tert-butyl ester To a solution of 0.250 g (4R,9aR)-7-[2-(tert-Butyl-dimethyl-silanyloxy)-1-hydroxy-ethyl]-6-[dimethyl-(1,1,2-trimethyl-propyl)-silanyloxymethyl]-4-methyl-3,4,9,9a-tetrahydro-1H-2,4a,5-triaza-fluorene-2-carboxylic acid tert-butyl ester in 4 ml dichloromethane was added at 0C 0.017 ml Huenigs base and 0.04 ml methanesulfonyl chloride. The mixture was stirred at this temperature for 30 min. and then quenched with 10% aqueous citric acid. The phases were separated and the organic phase was purified by chromatography on silica gel with heptane:ethyl acetate=9:1 to yield 0.167 g of the title compound as colorless oil. (MS: 619.5 (M+H$^+$))

Example 26

(4R,11aR)-4-Methyl-1,3,4,6,8,9,11,11a-octahydro-2H-7-oxa-2,4a,5-triaza-benzo[b]fluorene The title compound was obtained in analogy to example 9b starting from (4R,9aR)-6-[2-(tert-butyl-dimethyl-silanyloxy)-ethyl]-7-formyl-4-methyl-3,4,9,9a-tetrahydro-1H-2,4a,5-triaza-fluorene-2-carboxylic acid tert-butyl ester as slightly yellow oil (MS: 246.4 (M+H$^+$))

The starting material (4R,9aR)-6-[2-(tert-butyl-dimethyl-silanyloxy)-ethyl]-7-formyl-4-methyl-3,4,9,9a-tetrahydro-1H-2,4a,5-triaza-fluorene-2-carboxylic acid tert-butyl ester was obtained by the following sequence of steps.

Step 1

To a solution of 4.00 g (4R,9aR)-6-bromo-4-methyl-3,4,9,9a-tetrahydro-1H-2,4a,5-triaza-fluorene-2-carboxylic acid tert-butyl ester in 100 ml toluene was added drop wise at –78° C. 10.86 ml of a 1.5M solution of tert-butyllithium in pentane. The mixture was stirred at this temperature for 30 min. To the resulting solution was added 5.017 g (tert-butyldimethylsilyloxy) acetaldehyde and the mixture was stirred at –78° C. for 30 min. The reaction was quenched by addition of 10% aqueous ammonium chloride. The phases were separated and the organic phase was purified by chromatography on silica gel with heptane:ethyl acetate=4:1 to yield 2.34 g (4R,9aR)-6-[2-(tert-butyl-dimethyl-silanyloxy)-1-hydroxy-ethyl]-4-methyl-3,4,9,9a-tetrahydro-1H-2,4a,5-triaza-fluorene-2-carboxylic acid tert-butyl ester as slightly yellow oil (MS: 464.4 (M+H$^+$))

Step 2

(4R,9aR)-6-[2-(tert-butyl-dimethyl-silanyloxy)-ethyl]-4-methyl-3,4,9,9a-tetrahydro-1H-2,4a,5-triaza-fluorene-2-carboxylic acid tert-butyl ester To a solution of 0.70 g (4R,9aR)-6-[2-(tert-butyl-dimethyl-silanyloxy)-1-hydroxy-ethyl]-4-methyl-3,4,9,9a-tetrahydro-1H-2,4a,5-triaza-fluorene-2-carboxylic acid tert-butyl ester in 10 ml dichloromethane was added at room temperature 0.794 g tetrabromo methane and 0.628 g triphenylphosphine and the mixture was stirred at this temperature for 30 min. The reaction mixture was purified by chromatography on silica gel with heptane:ethyl acetate=2:1. The product (0.66 g) was taken up in 10 ml tetrahydrofuran. To the resulting solution was added a solution of 0.218 g potassium fluoride in 2 ml water, 0.028 g palladium acetate and 0.50 ml polymethylhydroxysilane and the mixture was stirred at room temperature for 3 h. The reaction mixture was partitioned between water and ethyl acetate, the phases were separated, the organic phase was washed with water and brine dried over sodium sulfate and evaporated. The residue was purified by chromatography on silica gel with heptane:ethyl acetate=2:1 to yield 0.329 g (4R,9aR)-6-[2-(tert-Butyl-dimethyl-silanyloxy)-ethyl]-4-methyl-3,4,9,9a-tetrahydro-1H-2,4a,5-triaza-fluorene-2-carboxylic acid tert-butyl ester as slightly yellow oil (MS: 448.5 (M+H$^+$))

Step 3

In analogy to example 1 the product of the previous step was converted to (4R,9aR)-6-[2-(tert-butyl-dimethyl-silanyloxy)-ethyl]-7-formyl-4-methyl-3,4,9,9a-tetrahydro-H-2,4a,5-triaza-fluorene-2-carboxylic acid tert-butyl ester (MS: 476.5 (M+H$^+$)).

Example 27

(4R,8R,11aR)-4,9-Dimethyl-1,2,3,4,6,9, 11,11a-octahydro-7H-8-oxa-2,4a,5-triaza-benzo[b]fluorene Application of the methodology detailed in example 1 and 9b to (4R,9aR)-6-[2-(tert-butyl-dimethyl-silanyloxy)-1-hydroxy-ethyl]-4-methyl-3,4,9,9a-tetrahydro-1H-2,4a,5-triaza-fluorene-2-carboxylic acid tert-butyl ester led to a mixture of the title compound and its five ring isomer (example 29) which was separated by chromatography on silica gel with dichloromethane:methanol:ammonia=90:10:1. to yield the pure title compound as colorless oil (MS: 262.3 (M+H$^+$)).

Example 28

(4R,8S,11aR)-4,9-Dimethyl-1,2,3,4,6,9,11,11a-octahydro-7H-8-oxa-2,4a,5-triaza-benzo[b]fluorene The title compound was obtained from (4R,9aR)-6-[2-(tert-butyl-dimethyl-silanyloxy)-1-methoxy-ethyl]-4-methyl-3,4,9,9a-tetrahydro-1H-2,4a,5-triaza-fluorene-2-carboxylic acid tert-butyl ester in analogy to example 26 as a colorless foam (MS: 276.3 (M+H$^+$) 244.4 (M+H$^+$-HOMe)).

The starting material was obtained from (4R,9aR)-6-[2-(tert-butyl-dimethyl-silanyloxy)-1-hydroxy-ethyl]-4-methyl-3,4,9,9a-tetrahydro-1H-2,4a,5-triaza-fluorene-2-carboxylic acid tert-butyl by alkylation with methyl iodide in dimethylformamide in the presence of sodium hydride and purified by chromatography on silica gel with heptane:ethyl acetate as colorless oil (MS: 478.5 (M+H$^+$)).

Example 29

((3R,5R,8aR)-5-Methyl-1,3,5,6,7,8,8a,9-octahydro-2-oxa-4,4b,7-triaza-cyclopenta[b]fluoren-3-yl)-methanol Application of the methodology detailed in example 1 and 9b to (4R,9aR)-6-[2-(tert-butyl-dimethyl-silanyloxy)-1-hydroxy-ethyl]-4-methyl-3,4,9,9a-tetrahydro-1H-2,4a,5-triaza-fluorene-2-carboxylic acid tert-butyl ester led to a mixture of the title compound and its six ring isomer (example 27) which was separated by chromatography on silica gel with dichloromethane:methanol:ammonia=90:10:1. to yield the pure title compound as colorless oil (MS: 262.0 (M+H$^+$)).

Example 30

(3R,5R,8aR)-3-Methoxymethyl-5-methyl-1,3,5,6,7,8,8a,9-octahydro-2-oxa-4,4b,7-triaza-cyclopenta[b]fluorene The title compound was obtained from the product of example 29 by first protection as Boc derivative, alkylation in dimethylformamide with methyl iodide in the presence of sodium hydride, removal of the Boc protective group with trifluoroacetic acid and purification by chromatography on silica gel with dichloromethane:methanol:ammonia=90:10:1. as slightly brownish oil (MS: 276.1 (M+H$^+$)).

Example 31

(5R,8aR)-2-Cyclopropyl-5-methyl-2,3,5,6,7,8,8a,9-octahydro-1H-2,4,4b,7-tetraaza-cyclopenta[b]fluorene To a solution of 0.014 g 2-cyclopropyl-5-methyl-5,6,7,8,8a,9-hexahydro-2H-2,4,4b,7-tetraaza-cyclopenta[b]fluorene in 1.0 ml glacial acetic acid and 1.00 ml water was added 0.005 g palladium 10% on charcoal and the mixture stirred for 18 h under 1 atmosphere of hydrogen at room temperature. The solvents were evaporated and the residue was purified by chromatography on silica gel with dichloromethane:methanol:ammonia=90:10:1 to yield 0.0025 g of the title compound as slightly brownish oil (MS: 271.3 (M+H$^+$)).

Example 32

(5R,8aR)-2-Cyclopropyl-5-methyl-5,6,7,8,8a,9-hexahydro-2H-2,4,4b,7-tetraaza-cyclopenta[b]fluorene A solution of 0.040 g (4R,9aR)-6-[(tert-butoxycarbonyl-cyclopropyl-amino)-methyl]-7-formyl-4-methyl-3,4,9,9a-tetrahydro-1H-2,4a,5-triaza-fluorene-2-carboxylic acid tert-butyl ester in 0.50 ml trifluoroacetic acid was kept at room temperature for 18 h. The solvent was evaporated and the residue was purified by chromatography on silica gel with dichloromethane:methanol:ammonia=90:10:1 to yield 0.0025 g of the title compound as colorless foam (MS: 269.4 (M+H$^+$)).

The starting material was obtained from (4R,9aR)-6-hydroxymethyl-4-methyl-3,4,9,9a-tetrahydro-1H-2,4a,5-triaza-fluorene-2-carboxylic acid tert-butyl ester by the following sequence of steps Step 1: (4R,9aR)-7-Bromo-6-bromomethyl-4-methyl-3,4,9,9a-tetrahydro-1H-2,4a,5-triaza-fluorene-2-carboxylic acid tert-butyl ester To a solution of 0.400 g (4R,9aR)-7-bromo-6-hydroxymethyl-4-methyl-3,4,9,9a-tetrahydro-1H-2,4a,5-triaza-fluorene-2-carboxylic acid tert-butyl ester (example 21 step 1) in 5 ml dichloromethane was added at room temperature 0.4 g triphenylphosphine and carbontetrabromide and the mixture was stirred at room temperature for 30 min. The red-orange solution was purified by chromatography on silica gel with heptane:ethyl acetate=1:1. The product fractions were collected and evaporated. The resulting oil (showing crystal seeds) was triturated with hexane. The crystalline solid was collected and dried to constant weight to yield 0.307 g of the title compound (MS: 406.1; 404.2 (M+H$^+$)).

53

Step 2

(4R,9aR)-7-Bromo-6-[(tert-butoxycarbonyl-cyclopropyl-amino)-methyl]-4-methyl-3,4,9,9a-tetrahydro-1H-2,4a,5-triaza-fluorene-2-carboxylic acid tert-butyl ester To a solution of 1.00 g (4R,9aR)-7-Bromo-6-bromomethyl-4-methyl-3,4,9,9a-tetrahydro-1H-2,4a,5-triaza-fluorene-2-carboxylic acid tert-butyl ester in 100 ml tetrahydrofuran was added 5.00 ml cyclopropylbamine and the mixture was kept at room temperature for 18 h. The solvent was evaporated and the residue was partitioned between water and ethyl acetate. The pH of the mixture was adjusted to 1.00 by addition of 2N hydrochloric acid. The phases were separated and the aqueous phase was mixed with dichloromethane. The ph of the mixture was adjusted to 12.00 by addition of 2n sodium hydroxide. The phases were separated and the organic phase was dried with sodium sulfate and evaporated. The residue was taken up in 20 ml dichloromethane and treated with 1.00 g di(tert-butyl)dicarbonate at room temperature for 4 h. The solvent was evaporated and the residue was purified by chromatography on silica gel with heptane:ethyl acetate=4:1 to yield 1.129 g of the title compound as colorless oil (MS: 539.; 537.4 (M+H$^+$)).

Step 3

(4R,9aR)-6-[(tert-Butoxycarbonyl-cyclopropyl-amino)-methyl]-7-formyl-4-methyl-3,4,9,9a-tetrahydro-1H-2,4a,5-triaza-fluorene-2-carboxylic acid tert-butyl ester To a solution of 0.847 g (4R,9aR)-7-bromo-6-[(tert-butoxycarbonyl-cyclopropyl-amino)-methyl]-4-methyl-3,4,9,9a-tetrahydro-1H-2,4a,5-triaza-fluorene-2-carboxylic acid tert-butyl ester in 30 ml toluene was added at −78° C. 1.5 ml of a 1.5M solution of tert-butyllithium and the mixture was stirred at this temperature for 10 min. To the resulting mixture was added 2.00 ml dimethylformamide and the mixture was stirred at −78° C. for 1 h and at 0° C. for 30 min. The reaction was quenched by addition of 10% aqueous citric acid. The phases were separated and the organic phase was purified by chromatography on silica gel with heptane:ethyl acetate=1:1 to yield 0.200 g of the title compound as orange yellow solid. (MS: 487.3 (M+H$^+$)).

Example 33

(5R,8aR)-5-Methyl-1,3,5,6,7,8,8a,9-octahydro-2-thia-4,4b,7-triaza-cyclopenta[b]fluorene To a solution of 0.046 g (5R,8aR)-5-Methyl-5,6,7,8,8a,9-hexahydro-2-thia-4,4b,7-triaza-cyclopenta[b]fluorene A solution of 0.270 g (4R,9aR)-7-formyl-4-methyl-6-tritylsulfanylmethyl-3,4,9,9a-tetrahydro-1H-2,4a,5-triaza-fluorene-2-carboxylic acid tert-butyl ester in 5 ml 90% aqueous formic acid was kept at room temperature for 6 h. The reaction mixture was partitioned between water and ethyl acetate. The phases were separated and the aqueous phase was mixed with dichloromethane. The pH of the mixture was adjusted to 12.00 by addition of 2N aqueous sodium hydroxide and the phases were separated. The organic phase was evaporated and the residue was purified by chromatography on silica gel with dichloromethane:methanol:ammonia=90:10:1 to yield 0.092 g of the title compound as brownish solid (MS: 246.3 (M+H$^+$)).

54

Example 34

(5R,8aR)-5-Methyl-5,6,7,8,8a,9-hexahydro-2-thia-4,4b,7-triaza-cyclopenta[b]fluorene A solution of 0.270 g (4R,9aR)-7-formyl-4-methyl-6-tritylsulfanylmethyl-3,4,9,9a-tetrahydro-1H-2,4a,5-triaza-fluorene-2-carboxylic acid tert-butyl ester in 5 ml 90% aqueous formic acid was kept at room temperature for 6 h. The reaction mixture was partitioned between water and ethyl acetate. The phases were separated and the aqueous phase was mixed with dichloromethane. The pH of the mixture was adjusted to 12.00 by addition of 2N aqueous sodium hydroxide and the phases were separated. The organic phase was evaporated and the residue was purified by chromatography on silica gel with dichloromethane:methanol:ammonia=90:10:1 to yield 0.092 g of the title compound as brownish solid (MS: 246.3 (M+H$^+$)).

The starting material was obtained from (4R,9aR)-7-bromo-6-bromomethyl-4-methyl-3,4,9,9a-tetrahydro-1H-2,4a,5-triaza-fluorene-2-carboxylic acid tert-butyl ester by the following sequence of steps Step 1 (4R,9aR)-7-Bromo-6-mercaptomethyl-4-methyl-3,4,9,9a-tetrahydro-1H-2,4a,5-triaza-fluorene-2-carboxylic acid tert-butyl ester To a suspension of 0.90 g (4R,9aR)-7-bromo-6-bromomethyl-4-methyl-3,4,9,9a-tetrahydro-1H-2,4a,5-triaza-fluorene-2-carboxylic acid tert-butyl ester in 10 ml ethanol was added at room temperature 0.2 g thiourea and the mixture was stirred at ambient temperature for 5 h. To the resulting clear solution was added 1 ml of 2N aqueous sodium hydroxide and the mixture was heated to reflux for 3 h. The reaction mixture was cooled to room temperature and partitioned between water and ethyl acetate. The phases were separated and the organic phase was purified by chromatography on silica gel with heptane:ethyl acetate=9:1 to yield 0.51 g of the title compound as crystalline solid (MS: 414.1 and 416.2 (M+H$^+$)).

Step 2 (4R,9aR)-7-Bromo-4-methyl-6-tritylsulfanylmethyl-3,4,9,9a-tetrahydro-1H-2,4a,5-triaza-fluorene-2-carboxylic acid tert-butyl ester To a solution of 0.25 g of the product of step 1 in 5 ml dichloromethane was added 0.25 g tritylpyridinium tetrafluoroborate at room temperature and the mixture was stirred at this temperature for 2 h. The reaction mixture was purified by chromatography on silica gel with dichlorometha:ethyl aceate=19:1 to yield 0.39 g of the title compound as colorless foam (MS: 656.3 and 658,4 (M+H$^+$)).

Step 3 (4R,9aR)-7-Formyl-4-methyl-6-tritylsulfanylmethyl-3,4,9,9a-tetrahydro-1H-2,4a,5-triaza-fluorene-2-carboxylic acid tert-butyl ester To a solution of 0.39 g product of step 2 in 10 ml toluene was dropwise added 1.0 ml of a 1.7 M solution of tert-butyl-lithium in pentane at −78 C. The resulting orange solution was stirred at −78 C. for 15 min. to the resulting orange solution was added 1.00 ml dimethylformamide at −78 C. The initially read but soon bright yellow solution was stirred at −78 C. for 15 min and was then allowed to thaw to room temperature over 30 min. The reaction mixture was quenched with 10% aqueous ammonium chloride, the phases were separated and the organic phase was purified by chromatography on silica gel with dichloromethane:ethyl acetate=19:1. to yield 0.21 g of the title compound as colorless foam (MS: 606.4(M+H$^+$)).

Example 35

Tablets containing the following ingredients can be manufactured in a conventional manner:

| Ingredients | Per tablet |
| --- | --- |
| Compound of formula I | 10.0-100.0 mg |
| Lactose | 125.0 mg |
| Maize starch | 75.0 mg |
| Talc | 4.0 mg |
| Magnesium stearate | 1.0 mg |

Example 36

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example 37

Injection solutions can have the following composition:

| Compound of formula I | 3.0 mg |
| --- | --- |
| Gelatine | 150.0 mg |
| Phenol | 4.7 mg |
| Water for injection solutions | ad 1.0 mL |

It is to be understood that the invention is not limited to the particular embodiments of the invention described above, as variations of the particular embodiments may be made and still fall within the scope of the appended claims.

The invention claimed is:

1. A compound of formula

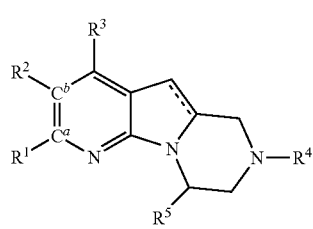

(I)

wherein $R^1$ and $R^2$ form together with the carbon atoms $C^a$ and $C^b$ to which they are attached

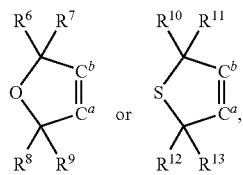

$R^3$ is hydrogen, alkyl or cycloalkyl;

$R^4$ is hydrogen, alkyl, cycloalkyl, alkylcarbonyl or cycloalkylcarbonyl;

$R^5$ is alkyl or cycloalkyl;

$R^6$ and $R^7$ are independently selected from hydrogen, alkyl, cycloalkyl, hydroxyalkyl and alkoxyalkyl;

$R^8$ and $R^9$ are independently selected from hydrogen, alkyl, cycloalkyl, hydroxyalkyl and alkoxyalkyl;

$R^{10}$ and $R^{11}$ are independently selected from hydrogen and alkyl; and $R^{12}$ and $R^{13}$ are independently selected from hydrogen and alkyl;

or pharmaceutically acceptable salts and esters thereof.

2. The compound according to claim 1, wherein the compound is of formula

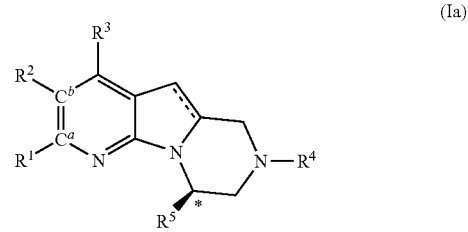

(Ia)

wherein the carbon atom C* to which $R^5$ is attached is of the R configuration and $R^1$ to $R^5$ are defined as in claim 1.

3. The compound according to claim 1, wherein the compound is of formula

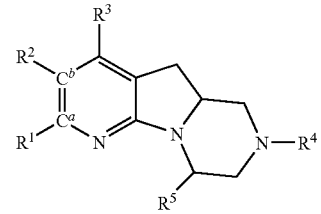

(II)

wherein $R^1$ $R^5$ are defined as in claim 1.

4. The compound according to claim 3, wherein the compound is of formula

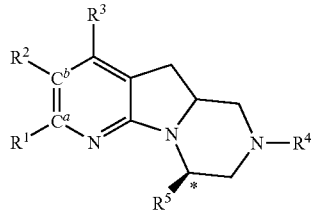

(IIa)

wherein the carbon atom C* to which $R^5$ is attached is of the R configuration and $R^1$ to $R^5$ are defined as in claim 1.

5. The compound according to claim 1, wherein the compound is of formula

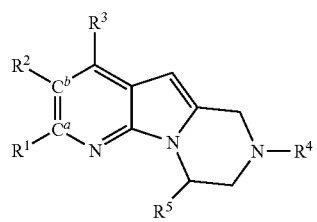

(III)

wherein $R^1$ $R^5$ are defined as in claim 1.

6. The compound according to claim 5, wherein the compound is of formula

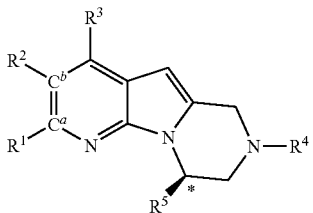

(IIIa)

wherein the carbon atom C* to which $R^5$ i is attached is of the R configuration and $R^1$ to $R^5$ are defined as in claim 1.

7. The compound according to claim 1, wherein $R^4$ is hydrogen, methyl, ethyl or methylcarbonyl.

8. The compound according to claim 7, wherein $R^4$ is hydrogen.

9. The compound according to claim 1, wherein $R^3$ is hydrogen.

10. The compound according to claim 1, wherein $R^5$ is methyl.

11. The compound according to claim 1, wherein $R^1$ and $R^2$ form together with the carbon atoms $C^a$ and $C^b$ to which they are attached

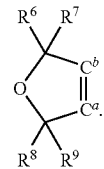

12. The compound according to claim 1, wherein $R^6$ and $R^7$ are independently selected from hydrogen and methyl.

13. The compound according to claim 1, wherein $R^8$ and $R^9$ are independently selected from hydrogen, methyl, ethyl, propyl, isopropyl and cyclopropyl.

14. The compound according to claim 1, wherein $R^{10}$, $R^{11}$, $R^{12}$ and $R^{13}$ are hydrogen.

15. The compound according to claim 1 selected from
(5R,8aR)-5-Methyl-1,3,5,6,7,8,8a,9-octahydro-2-oxa-4,4b,7-triaza-cyclopenta[b]fluorene;
(5R,8aS)-5-Methyl-1,3,5,6,7,8,8a,9-octahydro-2-oxa-4,4b,7-triaza-cyclopenta[b]fluorene;
(R)-5-Methyl-1,3,5,6,7,8-hexahydro-2-oxa-4,4b,7-triaza-cyclopenta[b]fluorene;
5-Methyl-1,3,5,6,7,8,8a,9-octahydro-2-oxa-4,4b,7-triaza-cyclopenta[b]fluorene;
(5R,8aR)-5,7-Dimethyl-1,3,5,6,7,8,8a,9-octahydro-2-oxa-4,4b,7-triaza-cyclopenta[b]fluorene;
(5R,8aR)-7-Ethyl-5-methyl-1,3,5,6,7,8,8a,9-octahydro-2-oxa-4,4b,7-triaza-cyclopenta[b]fluorene;
1-((5R,8aR)-5-Methyl-3,5,6,8,8a,9-hexahydro-1H-2-oxa-4,4b,7-triaza-cyclopenta[b]fluoren-7-yl)-ethanone;
(5R,8aR)-3,5-Dimethyl-1,3,5,6,7,8,8a,9-octahydro-2-oxa-4,4b,7-triaza-cyclopenta[b]fluorene;
(3S, 5R,8aR)-3,5-Dimethyl-1,3,5,6,7,8,8a,9-octahydro-2-oxa-4,4b,7-triaza-cyclopenta[b]fluorene;
(3R,5R,8aR)-3,5-Dimethyl-1,3,5,6,7,8,8a,9-octahydro-2-oxa-4,4b,7-triaza-cyclopenta[b]fluorene;
(3S,5R,8aR)-3-Ethyl-5-methyl-1,3,5,6,7,8,8a,9-octahydro-2-oxa-4,4b,7-triaza-cyclopenta[b]fluorene;
(3R,5R,8aR)-3-Ethyl-5-methyl-1,3,5,6,7,8,8a,9-octahydro-2-oxa-4,4b,7-triaza-cyclopenta[b]fluorene;
(3S,5R,8aR)-5-Methyl-3-propyl-1,3,5,6,7,8,8a,9-octahydro-2-oxa-4,4b,7-triaza-cyclopenta[b]fluorene;
(3R,5R,8aR)-5-Methyl-3-propyl-1,3,5,6,7,8,8a,9-octahydro-2-oxa-4,4b,7-triaza-cyclopenta[b]fluorene;
(3S,5R,8aR)-3-Isopropyl-5-methyl-1,3,5,6,7,8,8a,9-octahydro-2-oxa-4,4b,7-triaza-cyclopenta[b]fluorene;
(3R,5R,8aR)-3-Isopropyl-5-methyl-1,3,5,6,7,8,8a,9-octahydro-2-oxa-4,4b,7-triaza-cyclopenta[b]fluorene;
(3S,5R,8aR)-3-Cyclopropyl-5-methyl-1,3,5,6,7,8,8a,9-octahydro-2-oxa-4,4b,7-triaza-cyclopenta[b]fluorene;
(3R,5R,8aR)-3-Cyclopropyl-5-methyl-1,3,5,6,7,8,8a,9-octahydro-2-oxa-4,4b,7-triaza-cyclopenta[b]fluorene;
(5R,8aR)-3,3,5-Trimethyl-1,3,5,6,7,8,8a,9-octahydro-2-oxa-4,4b,7-triaza-cyclopenta[b]fluorene;
(5R,8aR)-1,5-Dimethyl-1,3,5,6,7,8,8a,9-octahydro-2-oxa-4,4b,7-triaza-cyclopenta[b]fluorene;
(5R,8aR)-1,1,5-Trimethyl-1,3,5,6,7,8,8a,9-octahydro-2-oxa-4,4b,7-triaza-cyclopenta[b]fluorene;
(5R,8aR)-1,3,5-Trimethyl-1,3,5,6,7,8,8a,9-octahydro-2-oxa-4,4b,7-triaza-cyclopenta[b]fluorene;
(5R,8aR)-1,1,3,3,5-Pentamethyl-1,3,5,6,7,8,8a,9-octahydro-2-oxa-4,4b,7-triaza-cyclopenta[b]fluorene;

(5R,8aR)-5,10-Dimethyl-1,3,5,6,7,8,8a,9-octahydro-2-oxa-4,4b,7-triaza-cyclopenta[b]fluorene;

((3R,5R,8aR)-5-Methyl-1,3,5,6,7,8,8a,9-octahydro-2-oxa-4,4b,7-triaza-cyclopenta[b]fluoren-3-yl)-methanol;

(3R,5R,8aR)-3-Methoxymethyl-5-methyl-1,3,5,6,7,8,8a,9-octahydro-2-oxa-4,4b,7-triaza-cyclopenta[b]fluorene;

(5R,8aR)-5-Methyl-1,3,5,6,7,8,8a,9-octahydro-2-thia-4,4b,7-triaza-cyclopenta[b]fluorene.

16. The compound according to claim 1 selected from (5R,8aR)-5-Methyl-1,3,5,6,7,8,8a,9-octahydro-2-oxa-4,4b,7-triaza-cyclopenta[b]fluorene;

(5R,8aR)-5,7-Dimethyl-1,3,5,6,7,8,8a,9-octahydro-2-oxa-4,4b,7-triaza-cyclopenta[b]fluorene;

(5R,8aR)-3,5-Dimethyl-1,3,5,6,7,8,8a,9-octahydro-2-oxa-4,4b,7-triaza-cyclopenta[b]fluorene;

(3S,5R,8aR)-3,5-Dimethyl-1,3,5,6,7,8,8a,9-octahydro-2-oxa-4,4b,7-triaza-cyclopenta[b]fluorene;

(3R,5R,8aR)-3,5-Dimethyl-1,3,5,6,7,8,8a,9-octahydro-2-oxa-4,4b,7-triaza-cyclopenta[b]fluorene;

(3S,5R,8aR)-3-Ethyl-5-methyl-1,3,5,6,7,8,8a,9-octahydro-2-oxa-4,4b,7-triaza-cyclopenta[b]fluorene;

(3S, 5R,8aR)-5-Methyl-3-propyl-1,3,5,6,7,8,8a,9-octahydro-2-oxa-4,4b,7-triaza-cyclopenta[b]fluorene;

(3S,5R,8aR)-3-Isopropyl-5-methyl-1,3,5,6,7,8,8a,9-octahydro-2-oxa-4,4b,7-triaza-cyclopenta[b]fluorene;

(3S,5R,8aR)-3-Cyclopropyl-5-methyl-1,3,5,6,7,8,8a,9-octahydro-2-oxa-4,4b,7-triaza-cyclopenta[b]fluorene;

(5R,8aR)-3,3,5-Trimethyl-1,3,5,6,7,8,8a,9-octahydro-2-oxa-4,4b,7-triaza-cyclopenta[b]fluorene;

(5R,8aR)-1,1,5-Trimethyl-1,3,5,6,7,8,8a,9-octahydro-2-oxa-4,4b,7-triaza-cyclopenta[b]fluorene; or (5R,8aR)-5-Methyl-1,3,5,6,7,8,8a,9-octahydro-2-thia-4,4b,7-triaza-cyclopenta[b]fluorene.

17. A pharmaceutical composition, comprising a therapeutically effective amount of a compound according to claim 1 and a therapeutically inert carrier.

* * * * *